(12) United States Patent
Awtar

(10) Patent No.: US 10,753,439 B2
(45) Date of Patent: Aug. 25, 2020

(54) TENSION MANAGEMENT APPARATUS FOR CABLE-DRIVEN TRANSMISSION

(71) Applicant: THE REGENTS OF THE UNIVERSITY OF MICHIGAN, Ann Arbor, MI (US)

(72) Inventor: Shorya Awtar, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 213 days.

(21) Appl. No.: 15/564,112

(22) PCT Filed: Apr. 4, 2016

(86) PCT No.: PCT/US2016/025926
§ 371 (c)(1),
(2) Date: Oct. 3, 2017

(87) PCT Pub. No.: WO2016/161449
PCT Pub. Date: Oct. 6, 2016

(65) Prior Publication Data
US 2018/0080533 A1 Mar. 22, 2018

Related U.S. Application Data

(60) Provisional application No. 62/142,980, filed on Apr. 3, 2015.

(51) Int. Cl.
*F16H 19/06* (2006.01)
*A61B 34/00* (2016.01)
(Continued)

(52) U.S. Cl.
CPC ......... *F16H 19/0672* (2013.01); *A61B 17/29* (2013.01); *A61B 34/71* (2016.02);
(Continued)

(58) Field of Classification Search
CPC ......... F16H 19/0672; F16H 2007/0844; F16H 2055/363; F16H 55/36; F16H 2019/0668;
(Continued)

(56) References Cited

U.S. PATENT DOCUMENTS 331,598 A * 12/1885 White ................. F16H 19/06
74/89.22
3,497,083 A  2/1970 Anderson et al.
(Continued)

FOREIGN PATENT DOCUMENTS

EP  3232951 A2  6/2016
EP  3232952 A1  6/2016
(Continued)

OTHER PUBLICATIONS

Awtar et al.; A minimally invasive surgical tool with enhanced dexterity and intuitive actuation; J. Med. Devices; 4(3); 8 pages; (Author's Draft; 12 pages); Sep. 10, 2010.
(Continued)

*Primary Examiner* — Jake Cook
*Assistant Examiner* — Gregory Robert Weber
(74) *Attorney, Agent, or Firm* — Shay Glenn LLP

(57) ABSTRACT

Slack-compensating pulleys, transmission systems including slack-compensating pulleys, and methods of operating these. In general, slack-compensating pulleys include a pulley body onto which a cable can wind, and one or more (e.g., two) slack take-up surfaces that rotate with the pulley body that are configured to remove slack form an outgoing length of cable by increasing the cable path length and wrap angle. In particular, described herein are minimal access tools having slack-compensating transmissions.

27 Claims, 25 Drawing Sheets

(51) Int. Cl.
*A61B 17/29* (2006.01)
*A61B 17/00* (2006.01)
*A61B 34/30* (2016.01)
*A61B 1/005* (2006.01)
*A61B 1/313* (2006.01)

(52) U.S. Cl.
CPC ........... *A61B 1/0057* (2013.01); *A61B 1/3132* (2013.01); *A61B 2017/00314* (2013.01); *A61B 2017/00323* (2013.01); *A61B 2017/291* (2013.01); *A61B 2017/2927* (2013.01); *A61B 2017/2929* (2013.01); *A61B 2034/306* (2016.02); *A61B 2034/715* (2016.02)

(58) Field of Classification Search
CPC ...... F16H 2007/0846; F16H 2007/0842; A61B 34/71; A61B 2034/715; A61B 1/0057; A61B 1/3132
USPC ............... 74/89.22, 490.04; 474/109; 901/21
See application file for complete search history.

(56) References Cited

U.S. PATENT DOCUMENTS

| | | | |
|---|---|---|---|
| 3,656,235 A | 4/1972 | Zuurveen | |
| 4,328,839 A | 5/1982 | Lyons et al. | |
| 4,466,649 A | 8/1984 | Ozawa | |
| 4,568,311 A | 2/1986 | Miyake | |
| 4,712,545 A | 12/1987 | Honkanen | |
| 4,750,475 A | 6/1988 | Yoshihashi | |
| 4,754,909 A | 7/1988 | Barker et al. | |
| 4,950,273 A | 8/1990 | Briggs | |
| 5,021,969 A | 6/1991 | Okamura et al. | |
| 5,069,596 A | 12/1991 | Mueller et al. | |
| 5,147,357 A | 9/1992 | Rose et al. | |
| 5,193,963 A | 3/1993 | McAffee et al. | |
| 5,209,747 A | 5/1993 | Knoepfler | |
| 5,297,443 A | 3/1994 | Wentz | |
| 5,317,952 A | 6/1994 | Immega | |
| 5,323,570 A | 6/1994 | Kuhlman et al. | |
| 5,330,502 A | 7/1994 | Hassler et al. | |
| 5,350,391 A | 9/1994 | Iacovelli | |
| 5,368,600 A | 11/1994 | Failla et al. | |
| 5,374,277 A | 12/1994 | Hassler | |
| 5,454,827 A | 10/1995 | Aust et al. | |
| 5,456,695 A | 10/1995 | Herve Dallemagne | |
| 5,549,637 A | 8/1996 | Crainich | |
| 5,599,151 A | 2/1997 | Daum et al. | |
| 5,619,195 A | 4/1997 | Allen et al. | |
| 5,620,415 A | 4/1997 | Lucey et al. | |
| 5,626,608 A | 5/1997 | Cuny et al. | |
| 5,683,412 A | 11/1997 | Scarfone | |
| 5,713,505 A | 2/1998 | Huitema | |
| 5,716,352 A | 2/1998 | Viola et al. | |
| 5,735,874 A | 4/1998 | Measamer et al. | |
| 5,782,748 A | 7/1998 | Palmer et al. | |
| 5,807,376 A | 9/1998 | Viola et al. | |
| 5,816,770 A * | 10/1998 | Itagaki ..................... | B25J 9/042 414/744.5 |
| 5,817,084 A | 10/1998 | Jensen | |
| 5,820,009 A | 10/1998 | Melling et al. | |
| 5,853,412 A | 12/1998 | Mayenberger | |
| 5,860,995 A | 1/1999 | Berkelaar | |
| 5,908,436 A | 6/1999 | Cuschieri et al. | |
| 6,042,555 A | 3/2000 | Kramer et al. | |
| 6,088,020 A | 7/2000 | Mor et al. | |
| 6,270,453 B1 | 8/2001 | Sakai | |
| 6,309,403 B1 | 10/2001 | Minor et al. | |
| 6,312,435 B1 | 11/2001 | Wallace et al. | |
| 6,330,837 B1 | 12/2001 | Charles et al. | |
| 6,714,839 B2 | 3/2004 | Salisbury et al. | |
| 6,853,879 B2 | 2/2005 | Sunaoshi | |
| 6,858,005 B2 | 2/2005 | Ohline et al. | |
| 6,889,116 B2 | 5/2005 | Jinno | |
| 6,994,716 B2 | 2/2006 | Jinno et al. | |
| 7,101,363 B2 | 9/2006 | Nishizawa et al. | |
| 7,147,650 B2 | 12/2006 | Lee | |
| 7,553,275 B2 | 6/2009 | Padget et al. | |
| 7,608,083 B2 | 10/2009 | Lee et al. | |
| 7,708,756 B2 | 5/2010 | Nobis et al. | |
| 7,736,254 B2 | 6/2010 | Schena | |
| 7,862,554 B2 | 1/2011 | Hegeman et al. | |
| 8,029,531 B2 | 10/2011 | Lee et al. | |
| 8,365,633 B2 | 2/2013 | Simaan et al. | |
| 8,425,408 B2 | 4/2013 | Boulais et al. | |
| 8,465,475 B2 | 6/2013 | Isbell | |
| 8,528,440 B2 | 9/2013 | Morley et al. | |
| 8,540,748 B2 | 9/2013 | Murphy et al. | |
| 8,551,076 B2 | 10/2013 | Duval et al. | |
| 8,603,135 B2 | 12/2013 | Mueller | |
| 8,668,702 B2 | 3/2014 | Awtar et al. | |
| 8,672,206 B2 | 3/2014 | Aranyi et al. | |
| 8,764,448 B2 | 7/2014 | Yang et al. | |
| 8,870,867 B2 * | 10/2014 | Walberg ................. | A61B 17/29 606/51 |
| 8,992,422 B2 | 3/2015 | Spivey et al. | |
| 9,161,771 B2 | 10/2015 | Steger | |
| 9,220,398 B2 | 12/2015 | Woodley et al. | |
| 9,629,682 B2 * | 4/2017 | Wallace ................. | A61B 5/042 |
| 9,629,689 B2 | 4/2017 | Bowles et al. | |
| 9,675,370 B2 | 6/2017 | Awtar et al. | |
| 9,696,700 B2 | 7/2017 | Beira et al. | |
| 9,814,451 B2 | 11/2017 | Sharma et al. | |
| 10,005,181 B2 * | 6/2018 | Hasegawa ............... | B25J 9/1612 |
| 10,085,624 B2 * | 10/2018 | Isoda ....................... | A61B 1/04 |
| 10,271,913 B2 * | 4/2019 | Yoshii ................. | F16H 19/0672 |
| 10,325,072 B2 | 6/2019 | Beira et al. | |
| 2001/0031983 A1 | 10/2001 | Brock et al. | |
| 2003/0036748 A1 | 2/2003 | Cooper et al. | |
| 2003/0135203 A1 | 7/2003 | Wang et al. | |
| 2003/0135204 A1 | 7/2003 | Lee et al. | |
| 2003/0176880 A1 | 9/2003 | Long et al. | |
| 2003/0176948 A1 | 9/2003 | Green | |
| 2004/0138700 A1 | 7/2004 | Cooper et al. | |
| 2004/0236316 A1 | 11/2004 | Danitz et al. | |
| 2004/0253079 A1 | 12/2004 | Sanchez | |
| 2005/0004431 A1 | 1/2005 | Kogasaka et al. | |
| 2005/0038469 A1 | 2/2005 | Lang | |
| 2005/0107667 A1 | 5/2005 | Danitz et al. | |
| 2006/0111210 A1 | 5/2006 | Hinman | |
| 2006/0111616 A1 | 5/2006 | Danitz | |
| 2006/0199999 A1 | 9/2006 | Ikeda et al. | |
| 2006/0259073 A1 | 11/2006 | Miyamoto et al. | |
| 2006/0282063 A1 | 12/2006 | Gotani | |
| 2007/0021738 A1 | 1/2007 | Hasser et al. | |
| 2007/0022562 A1 | 2/2007 | Hampton | |
| 2007/0078565 A1 | 4/2007 | Ghodoussi et al. | |
| 2007/0093790 A1 | 4/2007 | Downey et al. | |
| 2008/0039256 A1 | 2/2008 | Jinno et al. | |
| 2008/0065098 A1 | 3/2008 | Larkin | |
| 2008/0177285 A1 | 7/2008 | Brock et al. | |
| 2008/0243176 A1 * | 10/2008 | Weitzner .............. | A61B 1/0014 606/206 |
| 2009/0118044 A1 * | 5/2009 | Kuo ..................... | F16H 7/1281 474/109 |
| 2009/0171147 A1 | 7/2009 | Lee et al. | |
| 2009/0192511 A1 | 7/2009 | Haffenreffer | |
| 2010/0004606 A1 | 1/2010 | Hansen et al. | |
| 2010/0016853 A1 | 1/2010 | Burbank | |
| 2010/0030018 A1 | 2/2010 | Fortier et al. | |
| 2010/0056863 A1 | 3/2010 | Dejima et al. | |
| 2010/0234831 A1 | 9/2010 | Hinman et al. | |
| 2010/0249497 A1 | 9/2010 | Peine et al. | |
| 2011/0024145 A1 | 2/2011 | Click et al. | |
| 2011/0118707 A1 | 5/2011 | Burbank | |
| 2011/0152881 A1 | 6/2011 | Conner et al. | |
| 2011/0152922 A1 | 6/2011 | Jeong | |
| 2012/0095298 A1 | 4/2012 | Stefanchik et al. | |
| 2012/0118097 A1 | 5/2012 | Ilch | |
| 2012/0152055 A1 | 6/2012 | Lechuga Priego | |
| 2012/0186383 A1 | 7/2012 | Schvalb et al. | |
| 2012/0277762 A1 | 11/2012 | Lathrop et al. | |
| 2013/0012958 A1 | 1/2013 | Marczyk et al. | |

(56) References Cited

U.S. PATENT DOCUMENTS

| | | |
|---|---|---|
| 2013/0023868 A1 | 1/2013 | Worrell et al. |
| 2013/0066334 A1 | 3/2013 | Schoepp |
| 2013/0172860 A1 | 7/2013 | Szewczyk et al. |
| 2013/0239734 A1 | 9/2013 | Hinman |
| 2014/0135805 A1 | 5/2014 | Windgassen et al. |
| 2014/0331798 A1* | 11/2014 | Shim .................. B25J 9/104 74/89.22 |
| 2014/0371532 A1 | 12/2014 | Trovato |
| 2015/0021068 A1 | 1/2015 | Bernhardt et al. |
| 2015/0053455 A1 | 2/2015 | Hagi |
| 2015/0164601 A1 | 6/2015 | Sholev |
| 2015/0230697 A1 | 8/2015 | Phee et al. |
| 2016/0135830 A1 | 5/2016 | Volkmer et al. |
| 2016/0256232 A1 | 9/2016 | Awtar et al. |
| 2017/0095922 A1 | 4/2017 | Licht et al. |
| 2017/0097035 A1 | 4/2017 | Zimmerman et al. |
| 2017/0245954 A1 | 8/2017 | Beira |
| 2017/0360522 A1 | 12/2017 | Beira et al. |
| 2018/0000318 A9 | 1/2018 | Rogers et al. |
| 2018/0125519 A1 | 5/2018 | Beira et al. |
| 2018/0125592 A1 | 5/2018 | Beira |
| 2019/0133698 A1 | 5/2019 | Beira et al. |
| 2019/0336230 A1 | 11/2019 | Awater et al. |

FOREIGN PATENT DOCUMENTS

| | | | |
|---|---|---|---|
| EP | 3232973 A1 | | 6/2016 |
| EP | 3232974 A2 | | 6/2016 |
| EP | 3232977 A1 | | 6/2016 |
| EP | 3340897 A1 | | 3/2017 |
| GB | 973587 A | | 10/1964 |
| GB | 2513326 A | | 10/2014 |
| JP | 3-292879 A | | 12/1991 |
| JP | 8-84702 A | | 4/1996 |
| JP | H09-96146 A | | 4/1997 |
| JP | H09-96146 A | * | 4/1997 |
| JP | 2002102248 A | | 4/2002 |
| JP | 2003061969 A | | 3/2003 |
| JP | 2007130485 A | | 5/2007 |
| JP | 2009127289 A | | 6/2009 |
| JP | 6220085 B2 | | 10/2017 |
| WO | WO2006/036067 A2 | | 4/2006 |
| WO | WO2007/137304 A2 | | 11/2007 |
| WO | WO2007/146894 A2 | | 12/2007 |
| WO | WO2008/020964 A2 | | 2/2008 |
| WO | WO2013/027203 A1 | | 2/2013 |
| WO | WO2014/033717 A1 | | 3/2014 |
| WO | WO2015/125140 A1 | | 8/2015 |
| WO | WO2016/063213 A1 | | 4/2016 |
| WO | WO2016/161449 A1 | | 10/2016 |

OTHER PUBLICATIONS

Clement et al.; Design of a Snake-Like Manipulator; Robotics and Autonomous Systems; 6(3); pp. 265-282; Jul. 1990.

Do et al.; Adaptive control of position compensation for cable-conduit mechanisms used in flexible surgical robots; Proceedings of the 11th International Conference on Informatics in Control, Automation and Robotics (ICINCO-2014); IEEE; pp. 110-117; Sep. 1, 2014.

Ikuta et al.; Shape Memory Alloy Servo Actuator System With Electric Resistance Feedback and Application for Active Endoscope (conf. paper); 1988 IEEE Int'l Conf. on Robotics and Automation; pp. 427-430; Apr. 24-29, 1988.

Jug et al.; The JPL Serpentine Robot: a 12 DOF System for Inspection (Conference Paper); Proceedings—IEEE International Conference on Robotics and Automation 3: 5 pgs.; Jun. 1995.

Peirs et al.; A flexible distal tip with two degrees of freedom for enhanced dexterity in endoscopic robot surgery; MME'02; The 13th Micromechanics Europe Workshop; Sinaia, Romania; pp. 271-274; Oct. 6-8, 2002.

Simaan et al.; A dexterous system for laryngeal surgery; Proceedings of the 2004 IEEE International Conference on Robotics and Automation; New Orleans, LA.; pp. 351-357; Apr. 2004.

Walker et al.; Novel 'Elephant"s Trunk' Robot; IEEE/ASME International Conference on Advanced Intelligent Mechatronics, AIM; Piscataway, NJ, United States; pp. 410-415; Sep. 19-23, 1999.

Wikipedia; Constant Velocity Joint; 6 pgs.; retrieved from the internet (https://en.wikipedia.org/wiki/Constant-velocity_joint) on Dec. 22, 2016.

Bowles et al.; U.S. Appl. No. 15/785,349 entitled "Attachment apparatus for remote access tools," filed Oct. 13, 2017.

Bowles et al.; U.S. Appl. No. 15/943,689 entitled "Handle mechanism providing unlimited roll," filed Apr. 2, 2018.

Zimmerman et al.; U.S. Appl. No. 15/946,612 entitled "End-effector jaw closure transmission systems for remote access tools," filed Apr. 5, 2018.

Wikipedia; Six-bar linkage; 2 pgs; retrieved from the internet (https://en.wikipedia.org/w/index.php?title=Six-bar_linkage&oldid=670945266) on Apr. 26, 2019.

* cited by examiner neutral position after rotation

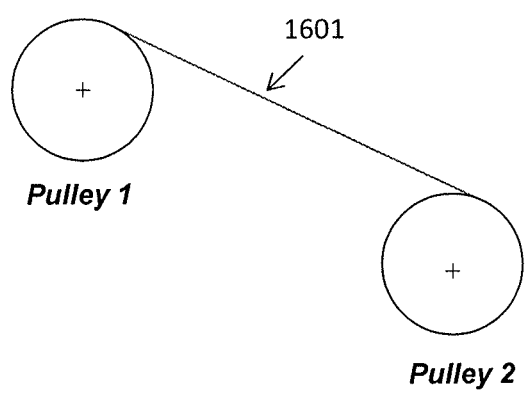
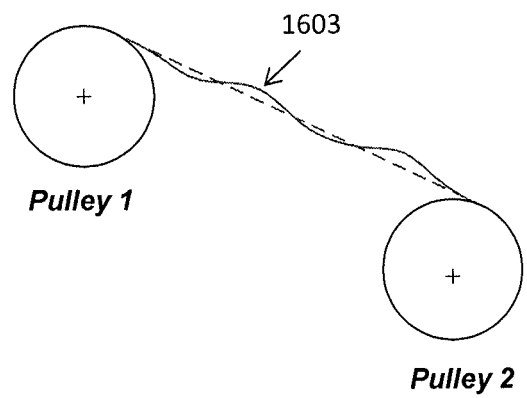
FIG. 16A  FIG. 16B
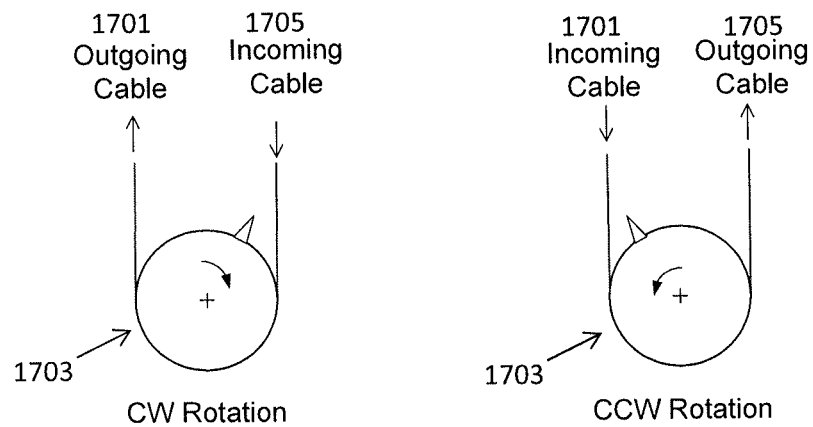
FIG. 17A  FIG. 17B

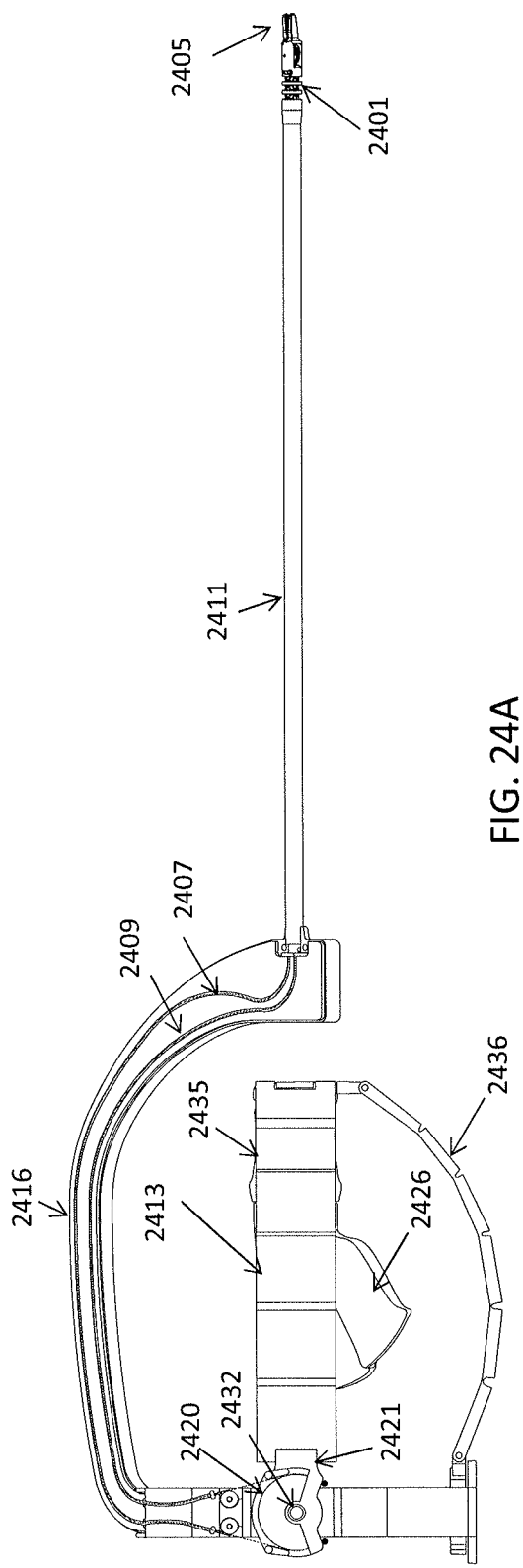
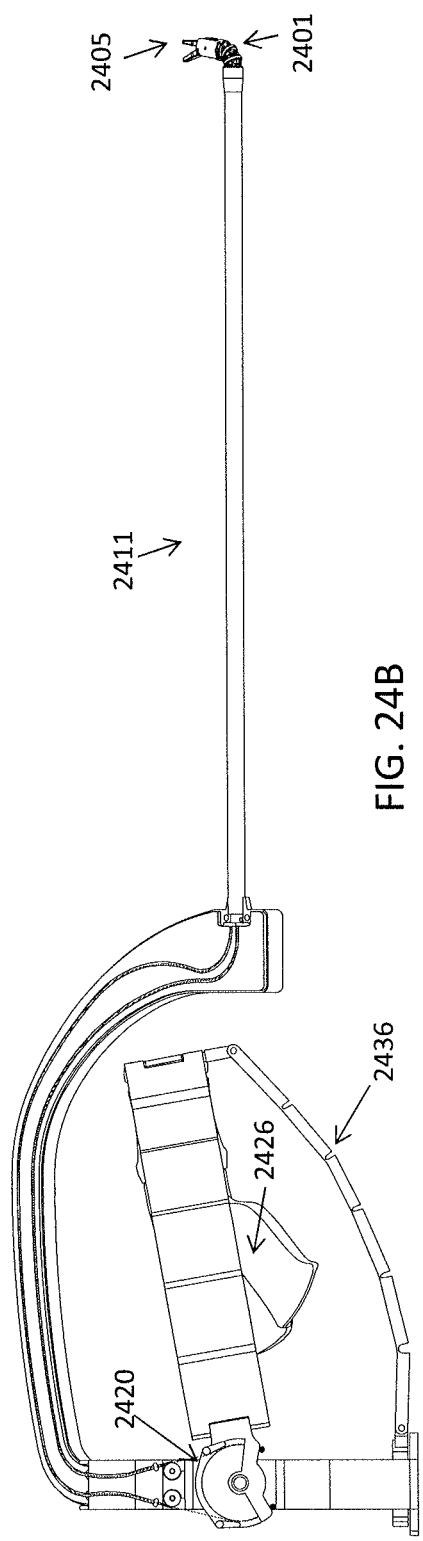
FIG. 24A
FIG. 24B

TENSION MANAGEMENT APPARATUS FOR CABLE-DRIVEN TRANSMISSION

CROSS REFERENCE TO RELATED APPLICATIONS

This application claims priority to U.S. Provisional Patent Application No. 62/142,980, filed on Apr. 3, 2015, titled "TENSION MANAGEMENT APPARATUS FOR CABLE-DRIVEN TRANSMISSION" which is herein incorporate by reference in its entirety.

This application may be related to U.S. patent application Ser. No. 14/166,503, filed on Jan. 28, 2014, and titled "MINIMAL ACCESS TOOL," Publication No. US-2014-0142595-A1, which is a continuation of U.S. patent application Ser. No. 12/937,523, filed on Apr. 13, 2009, titled "MINIMAL ACCESS TOOL," now U.S. Pat. No. 8,668,702, each of which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein are apparatuses for managing the cable tension and slack in a cable-driven transmission system and methods of operating them. In particular, described herein are slack take-up structures or features that may be combined with and/or integrated into one or more pulley of a cable-driven transmission system. In particular, the apparatuses and methods described herein may be used as part of a multi-link articulating end effector system.

BACKGROUND

Cable-driven transmissions may be used to transmit motion (typically rotation) from one location to another in many applications, including mechanical, robotic, and mechatronic applications. Given their small cross-sectional diameter, cables can be routed through any general circuitous path without taking up too much space. Some common applications that employ cable based transmission systems include consumer products such as printers and photocopiers as well as industrial systems such as gantries and material handlers. Further applications include robotic systems, medical devices, and other remote access devices.

Cables may include wires, ropes, strands, filaments, lines, tendons, pull-wires, etc. Cable driven transmission systems may typically rely on the tension that can be generated in a cable and transmitted via the cable. An example of a cable based transmission is shown in FIG. 1A. The driven pulley and the driving pulley are connected by two cables 307, 309 for bi-directional control (i.e. clockwise as well as counter clockwise). Depending on the actual construction, these two cables could be two distinct cables or a single cable that is continuously wrapped around both pulleys (e.g., having ends of the single cable that are interconnected). If the transmission is such that a pulley has to turn only over a partial rotation, then the cable may be locked to the pulleys via an engagement coupling such as a ferrule or crimp to avoid slippage.

When the driving pulley rotates counter clockwise (CCW) as shown in FIG. 1B, a tension may build on the left side cable 307 (which may be referred to as the transmitting cable). This tension may cause the driven pulley to also follow in the CCW direction. If there were no stretch in the cable, then the amount of cable pulled by the driving pulley on the left side 307 would be exactly equal to the amount of cable it releases on the right side 309. This would be considered a kinematically determinate transmission, and implies that the rotation of the driven pulley for a given rotation of the driving pulley is entirely dictated by the geometry of the overall system.

In reality this is generally not the case, as there is always some stretch in the region of cable on the left 307 because it is under tension, and because the cable has elasticity (i.e. it has some finite compliance along its length). Thus, the amount of cable pulled by the driving pulley on the left side may not be exactly equal to the amount of cable it releases on the right side. This results in the length of cable on the left side 307 being taut and the length of cable on the right side 309 being slack, as shown in FIG. 1B. In this example, there is no tension in the right side length of cable 309, and this transmission is no longer purely kinematic, because the rotation of the driven pulley for a given rotation of the driving pulley is dictated not only by the overall geometry of the system but also by the elastic properties of the cable. As a result, the driven pulley is no longer completely engaged with the driving pulley. For example, referring to FIG. 1B, if while holding the driving pulley fixed, if the driven pulley is perturbed in the clockwise direction 355, it would feel stiff. In other words, the driven pulley's rotation is determined or secured. However, if the driven pulley is perturbed in the CCW direction 357, it would feel compliant. Thus, the driven pulley rotation is not fully determined or secure. This lack of complete determinism of the driven pulley rotational position (which is sometimes also referred to as backlash, play, or slop) is a major drawback of cable driven transmission systems. Thus, there is a need for cable slack or tension management in cable driven transmission systems.

The direction of rotation of the driven pulley does not always have to be same as the direction of rotation of the driving pulley. The cable may be arranged in a slightly different manner, as shown in FIGS. 2A and 2B, such that a CCW rotation of the driving pulley produces a CW rotation of the driven pulley. Nevertheless, the above described problem of cable slack applies in this case as well.

In certain applications, this slack generation happens not just because of the elastic stretch of the cable, but also due to the geometry or kinematics of the transmission system. For example, in certain applications, mechanical and robotic tools often employ a controllably bendable elongate member. Such elongate members may be bent or articulated by cables, tendons, or pull-wires, and may allow bending in multiple directions. Unfortunately, when multiple cables (which may equivalently be wires, ropes, strands, filaments, lines, actuating cables, tendons, pull-wires, etc.) are used, bending in one direction, e.g., by pulling on one or more of the cables, may result in slack forming in the other cable(s). This slack may negatively impact the operation of the device, particularly when pulling/pushing the cables to control bending of the member, resulting in non-deterministic or unpredictable motion characterized by compliance or backlash.

One example of a controllably bendable elongate member includes a multi-link snake-like joint (also referred to as an end effector joint) that may provide articulated motion (i.e.

wrist-like dexterity, or rotation about two axes) to an end effector. Bending movements may be controlled by two or more cables (including pairs of cables) coupled to some or all of the links. The end effector might include one or more of a grasper, probe, pliers, mini-scissors, light source, catheters, etc., in medical and non-medical tools. Such tools may benefit from a large angular range of rotation at the end effector region to provide reach and work space. Depending on the application, the end effector may articulate only in one direction (e.g. pitch or yaw) or in two orthogonal directions (e.g. pitch and yaw).

An example of an end effector joint design that allows two orthogonal rotations is a multi-link end effector joint which comprises links, or disks, or elements, or link elements with an alternating sequence of pivots to provide the two desired wrist-like rotations (e.g., pitch and yaw), and is illustrated in FIG. 7. In this example, a pair of cables (719, 719' and 721, 721') is used per each end effector rotation direction, and these cables pass through holes 729, 731, etc. on the periphery of the links, resulting in an end-effector joint that has two rotations (e.g., pitch and yaw). End effector joints such as this that include multiple serially linked elements may be maneuverable like a snake; hence they may be sometimes referred to as "snake-like joints". Similarly, when link elements are serially connected via single-axis pivots (all aligned in one direction) only, the resulting device has an end effector rotational capability in a single plane, as illustrated in FIG. 8A. In this example, the "base link" 203 is attached to the tip or end of the tool (e.g., a medical device or a robotic arm). The "end link" 205 may be connected to an end effector (e.g., grasper, light, etc.) to provide the end effector with the desired articulation capability. The driving cables such as 719, 719', 721, and 721' are attached to/terminated at the end link but pass through the holes in the remaining links.

FIGS. 8A and 8B illustrate the problem with slack in the cable referred to above. When the elements or links forming the end effector device are serially linked via single-axis pivots all aligned in one direction only, the end effector rotation is limited to a single direction (pitch or yaw). Alternatively, when elements forming the articulating device are serially linked via pivots with alternating rotational axes perpendicular to each other, an end effector rotation capability may be possible in two rotational directions (pitch and yaw), as was shown in FIG. 7. Alternatively, elements forming the end effector joint may be serially linked, e.g., via ball and socket joints, which then provide three rotations (pitch, yaw, and roll) of the end effector. In all these cases, the end effector joint poses several design challenges. As an example, for rotation in any given plane (e.g. as shown in FIGS. 8A and 8B), it may be desirable to employ multiple links and pivots because this allows for a large range of rotational motion of the end link and in the associated work space. Also, by using multiple links and pivot joints, the rotation per link/joint is reduced, potentially resulting in a design that is more practical to manufacture and assemble, and that may operate at a smaller size scale. However, this design is inherently prone to problems associated with slack generation in the cables that are used for driving the end effector rotation discussed above. As shown in FIGS. 8A and 8B, upon rotating the pulley to operate on the first cable 207 to bend the device towards left, the geometry or kinematics of articulation is that the amount of cable 207 released on the left side may be greater than the amount of cable 209 pulled in on the right hand side, even when the cable elastic stretch is ignored.

When such a multi-link end effector joint is actuated by a driving pulley (either manually, mechanically, or via a motor, etc.) on the input end (or equivalently, the master end, user end, or control end) of an associated transmission cable, this typically produces a situation where the cable 307 on the left hand side remains taut while the cable on the right hand side 309 develops slack, as illustrated in FIGS. 9A and 9B. This situation may occur when the driving pulley rotates counter clock wise (CCW) and the end effector rotates to the left, as illustrated in FIG. 9B. This situation may be reversed when the end effector is actuated towards the right (i.e. rotating the pulley to turn clock-wise), and the right hand side cable 309 would be taut and the left hand side cable 307 will have slack.

In general it would be desirable to provide a simple solution to this problem, and particularly to provide a mechanical solution that does not require the use of additional sensors or powered actuators such as electric, pneumatic, or hydraulic motors or electronic/computer control. Thus, described herein are apparatuses, including tensioning pulleys incorporating and/or integrated with a slack take-up element that may address the issues raised above in cable-based transmission systems that may have slack due to either geometric/kinematic reasons (e.g. in case of driving a multi-link end-effector joint) or due to elastic reasons (e.g. compliance of cable and/or other transmission elements).

SUMMARY OF THE DISCLOSURE

Described herein are apparatuses and methods that compensate for slack in a cable of a transmission system having at least one pulley. In particular, these apparatuses and methods may compensate for slack in the transmission system by applying a tension to a cable, or equivalently removing slack from the cable, that is related to the rotation of a pulley that is operating on the cable. The slack-compensating pulleys described herein, and apparatuses including them, may lengthen the path taken by a part of a cable that would otherwise be slack, by increasing the wrap angle of the cable on the pulley body. The slack-compensating pulley apparatuses described herein may generally include a pulley body that includes a surface on which a cable may wrap at a wrap angle, and a slack take-up surface that rotates with the pulley body and applies tension to the cable when the pulley body rotates. The slack take-up surface may be part of or attached to a support that extends from the pulley body and rotates with the pulley body. Driving the slack take-up surface against a length of the cable that extends off of the pulley body when the pulley body is rotated increases the wrap angle of the cable around the pulley body and can reduce or eliminate slack in this portion of the cable. The slack-compensating pulleys described herein may include one or more than one (e.g., two, three, etc., but preferably two) slack take-up surfaces. Thus, a slack-compensating pulley may include one or more slack take-up surfaces that rotate with the pulley body of the slack-compensating pulley and deflect a portion of the cable to lengthen the cable path, and therefore increase the wrap angle of the cable around the pulley body, when the slack-compensating pulley rotates in a first direction about an axis of rotation of the slack-compensating pulley, but not when rotating in the opposite direction. When the slack-compensating pulley is rotated in the opposite direction, the slack take-up surface may be withdrawn from the cable, reducing the wrap angle of the cable around the pulley body and reducing the path length taken by the cable off of the pulley body.

The apparatuses described herein may be configured as devices and/or systems, including slack-compensating pulley apparatuses such as slack-compensating transmission, or apparatuses including slack-compensating transmissions. In particular, described herein are minimally invasive tools (e.g., minimal access tools) having slack-compensating transmissions.

Any of the apparatuses described herein may include a cable. The cable may be wrapped around the slack-compensating pulley and specifically may be wrapped around the pulley body portion of the slack-compensating pulley at a wrap angle. The cable may be held to the pulley body via friction or via a mechanical fixture so that the cable does not appreciably slide on the pulley. As used herein, a cable may be any elongate flexible member, e.g., wire, rope, strand, filament, strip, ribbon, lines, actuating cables, tendons, pull-wires, etc.). The wrap angle of the cable on the pulley body is generally less than 360 degrees (e.g., the cable does not wrap completely around the pulley body. For example, the wrap angle of the cable body when the pulley is not being actuated may be less than 360° (e.g., less than 359°, less than 340°, less than 320°, less than 300°, less than 280°, less than 260°, less than 240°, less than 220°, less than 200°, less than 180°, less than 160°, less than 140°, less than 120°, less than 100°, etc. or between 1° and 359°, etc.). An increase in the wrap angle caused by rotating a slack take-up surface in the same direction as a pulley body is shown in FIGS. 19A and 19B, and described in greater detail below. In this example, the wrap angle 1956 of the cable on the pulley body before rotating the driving pulley 1931 is shown in FIG. 19A to be approximately 180 degrees. Rotating the slack compensating pulley clockwise, as shown in FIG. 19B, drives the first slack take-up surface against the cable and increases the wrap angle 1956', shown here to be approximately 210 degrees).5

For example, described herein are slack-compensating pulley apparatuses for a transmission system. A slack-compensating pulley apparatus may include: a pulley body; a cable track along a surface of the pulley body on which a cable may wrap with a wrap angle; a support extending from the pulley body; and a slack take-up surface on the support, wherein the slack take-up surface is positioned radially outside of the surface of the pulley body so that a length of cable may extend between the pulley body and the slack take-up surface, wherein the support and slack take-up surface rotate with the pulley body to remove slack in the cable when the pulley body is rotated in a first direction by increasing the wrap angle of the cable on the pulley body.

Thus, any of the slack-compensating pulleys described herein may be used with (or as part of) a transmission that transmits motion, e.g., rotational motion, through one or more cables while removing or reducing slack in the one or more cables as the pulleys are operated. For example, a slack-compensating transmission may include a cable that is coupled to a slack-compensating pulley to remove slack from the cable when the slack-compensating pulley acts on the cable. The slack-compensating pulley generally includes one or more slack take-up surfaces that rotate with the pulley body of the slack-compensating pulley and deflect the cable to lengthen the cable path and increase the wrap angle around the pulley body when the slack-compensating pulley rotates in a first direction about an axis of rotation of the pulley, but not when rotating in the opposite direction. When the slack-compensating pulley is rotated in the opposite direction, the slack take-up surface withdraws from the cable, restoring or reducing the length of the path taken by the cable off of the pulley body and reducing the wrap angle.

Note that the slack take-up surface does not have to withdraw completely from the cable or restore the nominal path (as described below) when the pulley body is rotated to withdraw the slack take-up surface from the cable, but may remain against the cable. In some variations, however, the slack take-up surface is fully withdrawn from the cable.

The pulley body may be any appropriate shape, including circular, oval, nautilus, crescent-shaped, hemi- or semi-circular, etc. For example, a pulley body may be cylindrical, e.g., having a round cross-section, or may have a non-round (e.g., nautilus, oval, teardrop, C-shaped, etc.) cross-section. The pulley body may include a channel or path for the cable and/or a connection to an end of the cable. In general, the portion of the pulley body forming the cable track is continuous and may be curved. This portion may be on an outer surface of the pulley body, including around a portion of an outer perimeter of the pulley body. The cable track portion may extend all the way around the pulley body, or more typically only over a portion of the perimeter of the pulley body.

A cable track may include a path, channel, or region on a pulley body along which the cable may be held during operation of the slack-compensating pulley. The cable may be held on the cable track so that the cable can be pulled by the rotation of the pulley body. The cable track may be on an external surface of the pulley body. For example, the cable track may be on an external surface of the pulley body. For example, when the pulley body has a circular or semi-circular shape, the cable track may extend over the outer surface of the circular or semi-circular shape. In some variations the surface is internal or partially covered.

As mentioned, a support is typically coupled to the pulley body so that the two rotate together. The support may be an arm or plate that extends from the pulley body without crossing or interfering with the path that the cable take relative to the pulley body, except that for the attached slack take-up surface. A slack-compensating pulley may include one or more (e.g., two) slack take-up surfaces and when there are multiple slack take-up surfaces, each slack take-up surface may be attached to the same support or it may be attached to a separate support. The support may be rigid or flexible. In particular, the support may include or may be a biasing element such as a spring or elastic. If the support includes (or is entirely) a biasing element, then the slack take-up portion may adapt or adjust based on the deflection of the cable and the rotational position. The support (e.g., an extension, arm, etc.) may rigidly move with the pulley body, or it may flex or bend relatively to the pulley body. For example, the arm(s) may be spring-loaded so that they apply a varying force against the length of cable (legs) as they are rotated with the pulley body.

The slack take-up surface may be an integral part of the support or it may be separate and connected to the support. For example, the slack take-up surface may be a low-friction surface. A low-friction surface may include a coating, covering, or the like. Low-friction surfaces may be lubricious, and/or may include a wheel or other moving member against which the cable may freely slide or move. The slack take-up surface may project from the support, or they may be a region of the support. As will be described and illustrated below, the slack take-up surface may be a portion (e.g., an inner or outer surface) of the support (see, e.g., FIGS. 13A-13B and 14A-14B, described in greater detail, below), e.g., within a loop formed by the first arm.

The slack take-up surface may generally be positioned off of the outer (cable track) surface of the pulley body, e.g. at a radius that is greater than the radius of the cable track of the pulley body. The slack take-up surface may be held by the support so that the slack take-up surface does not contact the cable (and/or does not apply displacement to the cable) when the pulley is in a neutral position. The slack take-up surface may be positioned so that when the pulley is rotated in an appropriate direction (e.g., clockwise or counterclockwise) about the axis of rotation, the slack take-up surface may be moved into the path of the cable as it leaves the surface, e.g., the cable track, of the pulley body and deflects the cable from the nominal path, forming a longer cable path and increasing the wrap angle of the cable around the pulley body, and taking up slack in the cable.

In general, the slack take-up surface is positioned further radially outward from the axis of rotation than a region of the outer perimeter of the pulley body between the slack take-up surface and the axis of rotation. The portion of the cable leaving the pulley body may pass between is region of the outer perimeter of the pulley body and the slack take-up surface. There may be a minimum space between the slack take-up surface and the outer surface of the pulley body (which may be part of the cable track). This minimum space should be greater than the diameter of the cable, as the cable may be positioned between the outer diameter of the pulley body and the slack take-up surface.

In operation, the slack take-up surface may remove slack from a length of cable on one side of a pulley by deflecting the path that the portion of the cable coming off of the pulley body, e.g., off of the cable track on the pulley body, which increases the wrap angle of the cable around the pulley body and also lengthens the path taken by the cable off of the pulley path when the pulley is rotated in a first direction. Rotating the pulley in the opposite direction may shorten the length of the path taken by the cable off of the pulley body. The cable path may be described as longer relative to the nominal path length between the pulley body and a target such as a driven (e.g., follower) pulley or gear, an actuator, a mechanical slider, etc. or an intermediate structure such as an idler, or the like. Thus, the path that the cable travels without contacting another structure may be longer when the slack take-up surface is deflecting the cable than when it is not, thereby recuing slack in the cable, or the portion of the cable being deflected.

In any of these variations, the slack-compensating pulley apparatus may include a second slack take-up surface. The second slack take-up surface may also be positioned radially outside of the surface of the pulley body so that a second length of cable may extend between the pulley body and the second slack take-up surface. In general, the second slack take-up surface also rotates with the pulley body to remove and/or reduce slack in the cable when the pulley body is rotated in a second direction. For example, the slack-compensating pulley apparatus may include a second slack take-up surface on the support (the same support as the first slack take-up surface or a separate support) and the second slack take-up surface may be positioned radially outside of the surface of the pulley body so that a second length of cable may extend between the pulley body and the second slack take-up surface, wherein the support and second slack take-up surface rotate with the pulley body to remove and/or reduce slack in the cable when the pulley body is rotated in a second direction.

Any of the slack-compensating pulley apparatuses described herein may include a cable on the surface of the pulley body. The cable may have a first cable length extending in a first cable path that is tangent to the surface of the pulley body on a first side of the pulley body, wherein when the slack take-up surface rotates with the pulley body about an axis of rotation in the first direction, the slack take-up surface may be driven onto the first cable length on the first side of the pulley body and deflects the first cable length from the first cable path into a longer path, and when the pulley body is rotated in the axis of rotation in a second direction, the slack take-up surface may be withdrawn away from the first cable length on the first side of the pulley body to shorten the cable path.

In general, the slack take-up surface may be part of or attached to the support. For example, the support may comprise a plate extending from the pulley body parallel to and offset from a plane through the cable track. The support may include a protrusion that extends into the plane of the cable track around the pulley body and the slack take-up surface may be part of this protrusion or coupled to it. In some variations the protrusion is an arm or wing extending from the pulley body and the slack take-up surface is a part of or coupled to the arm or wing facing the cable. In some variations the slack take-up surface is an inner surface of a loop formed by the support.

In general, the support may be configured to rigidly move with the pulley body, however, in some variations the support comprises a bias element that is configured to allow the slack take-up surface to deflect relative to the pulley body when force is applied against the slack take-up surface by the cable.

A slack-compensating pulley apparatus may include: a pulley body; a cable track along a surface of the pulley body on which a cable may wrap; a support comprising a plate extending from the pulley body parallel to and offset from a plane through the cable track; and a protrusion comprising a slack take-up surface, the protrusion extending from the support, wherein the slack take-up surface is positioned radially outside of the surface of the pulley body so that a length of cable may extend between the pulley body and the slack take-up surface, wherein the support and the slack take-up surface rotate with the pulley body to remove and/or reduce slack in the cable when the pulley body is rotated in a first direction by lengthening a path taken by the cable.

The slack-compensating pulley apparatus may include a second slack take-up surface, wherein the second slack take-up surface is positioned radially outside of the surface of the pulley body so that a second length of cable may extend between the pulley body and the second slack take-up surface, wherein the second slack take-up surface rotates with the pulley body to remove and/or reduce slack in the cable when the pulley body is rotated in a second direction by lengthening a path taken by the cable off of the cable track, increasing the wrap angle of the cable on the pulley body.

A slack-compensating pulley apparatus for a transmission system may include: a pulley body having an axis of rotation; a cable wrapped around an outer surface of the pulley body at a wrap angle and having a first cable length extending in a first cable path that is tangent to the outer surface of the pulley body on a first side of the pulley body; a support extending from the pulley body; and a slack take-up surface on the support, wherein the slack take-up surface rotates with the pulley body so that when the pulley body is rotated about the axis of rotation in a first direction, the slack take-up surface is driven against the first cable length and deflects the first cable length from the first cable path into a longer path, increasing the wrap angle on the pulley body and removing slack, and when the pulley body is rotated in the axis of rotation in a second direction, the slack take-up surface is withdrawn away from the first cable length so that the first cable length travels in a shorter cable path reducing the wrap angle on the pulley body.

The pulley body may refer to the driving pulley body (though in some examples a second slack-compensating pulley apparatus may be incorporate a driven pulley connected by the cable to the driving pulley).

As used herein, the top of the pulley body generally refers to a point on the pulley body in the direction of travel of the cable or cables connecting to the pulley body, through which passes a line that bisects an angle projected by the two cables as they embrace (or extend from) the pulley body. For example, see FIGS. 19C-19E. In these examples, the top of each pulley body is determined based on the directions of the cables connecting to the pulley bodies. The angle β between the cables (see, e.g., FIGS. 19C and 19D), which may be found by projecting the lines in the direction of each cable as it approaches the pulley body. The intersection point of a line that bisects this angle (β) and the outer surface of the pulley body on the side of the pulley facing the direction that the cables extend in is the "top" of the pulley body. When, as shown in FIG. 19E, the cables extend in parallel from the pulley body, the top is the point on the outer surface in the direction facing the direction of the cables midway between the cables, shown by the line 1905 and top point 1903.

For example, in FIG. 1A, the top 151 is shown by the dial member (which may not be physically present in all embodiments). A line extending from the center of rotation 161 to the top 151 is parallel to both of the cables 307, 309 in this example.

Although many of the examples of slack-compensating pulley apparatuses described herein are generally symmetric (e.g., include an axis of symmetry, which may correspond to the bisecting line between the two cable connecting pathways at the pulley body) they do not have to be symmetric, including symmetric about this axis of symmetry through the top and center (and/or axis of rotation) of the pulley. In some examples, when the apparatus has two supports, the supports may be differently shaped and/or positioned, and/or the slack take-up surfaces may be differently shaped and/or positioned relative to each other. In addition, in some variations, the apparatus includes only a single slack-compensating member, for acting on only a single side, e.g., a single length of cable; an opposite cable may not be compensated.

In any of the slack-compensating pulley apparatuses described herein, the apparatus may include multiple slack take-up surfaces that may be held by a single support or a pair of supports. For example, a slack-compensating pulley apparatus for a transmission system may include: a pulley body; a cable track around the pulley body, the cable track configured to hold a cable; a first support extending from the pulley body and a second support extending from the pulley body; a first slack take-up surface on the first support and radially offset from the cable track of the pulley body, wherein the first slack take-up surface rotates with the pulley body to remove and/or reduce slack from the cable when the cable is on the cable track and the pulley body is rotated counterclockwise; and a second slack take-up surface on the second support and radially offset from the cable track of the pulley body, wherein the second slack take-up surface rotates with the pulley body to remove and/or reduce slack from the cable when the cable is on the cable track and the pulley body is rotated clockwise.

As mentioned, the one or more supports for the first and/or second slack take-up surfaces are generally coupled to the pulley body (either directly or indirectly) so the support and slack take-up surface rotates with the pulley.

Thus, the support may be rigidly coupled to the pulley body to rotate with the pulley body through a predetermined range of rotation (typically between +/−90 degrees). The support may be an arm, wing or extension from the pulley body, or it may be a plane, surface, flange, or board extending from the pulley body. This support may be rigid or flexible. The support may be a disk or ring (annular ring) around all or part of the pulley body. For example, when the support comprises a ring or disk around the pulley body, the support may extend in a plane approximately parallel to but offset from the cable track around the pulley body.

The support may typically extend from the pulley body so that it rotates with the pulley body but does not modify the cable path on the outer surface of the pulley body. For example the support may extend from the top of the pulley body. In some variations, the cable track of the cable on the outer surface of the pulley body extends around the pulley body and through an opening in the support(s) (e.g., the first support). The support may be referred to as an extension, wing, arm, plate, ring, etc. that extends radially outward relative to the outer surface of the pulley body and is configured to rotate with the pulley body.

In general, the slack take-up surfaces that apply slack-compensation (e.g., tension) to a cable operated on by the pulley body may be tabs, rollers, pegs, pins, or the like. In general, these slack take-up surfaces may have a relatively low friction surface for interacting with the cable. For example the slack take-up surface may be smooth, and/or treated to minimize friction (e.g., minimize the resistance between the cable and the slack take-up surface, as the cable may be moving against the slack take-up surface by operation of the pulley body). In some variations the slack take-up surface is a roller (e.g., rolling surface), allowing rolling of the slack take-up surface in the direction of motion of the cable. The slack take-up surface may be connected to the support by a rigid connection or by a compliant and/or biased connection (e.g., spring, etc.). In some variation the support is itself compliant, having spring-like properties. Thus, the slack-compensating elements, including the slack take-up surface and/or the support may limit the amount of force applied to the cable as the pulley body rotates, driving the slack take-up surface into the cable.

The slack take-up surface is generally held by the support so that it is located radially outward from the pulley body (e.g., within some predetermined distance from the outer surface of the pulley body, e.g., between just past the outer surface and a multiple of the radius of the pulley body, e.g., 0.1×, 0.2×, 0.3×, 0.4×, 0.5×, 1×, 1.5×, 2×, 2.5×, 3×, 4×, 5×, etc.). The slack take-up surface is also generally located around the pulley body in (or adjacent to) the path of the cable extending from the pulley body, and may be located around the outer surface at an angle of between about 0 and about 90 degrees (or −90 degrees) relative to the center of rotation and the top of the pulley body. For example, the slack take-up surface may be located within an angle between a line extending from the first slack take-up surface and the center point and the line extending from the top of the pulley body and the center point is between about 5 and 90 degrees, between about 10 and 90 degrees, between about 15 and 90 degrees, between about 20 and 90 degrees, between about 25 and 90 degrees, etc.

A cable may contact the pulley body initially at a cable contact point on the outer surface of the pulley body. FIG. 19B shows the contact sites for each length of cable 1921, 1922. Once on the pulley body, the cable may rest on an outer surface (e.g., groove, lip, rim, strip, etc.) and be wound on/off the cable body from this surface. In general the slack-compensating apparatus is configured so that the support member does not interfere with the movement of the cable on the pulley body, and thus may be separated from the cable track of the cable on the pulley body (and/or may include openings or passages through the support).

Also described herein are methods of removing slack from a transmission system. A method may include the use of any of the apparatuses described herein (and similarly, an apparatus may be configured to perform any of the methods described herein). In general, a method may include removing slack from a length of cable operated on by a pulley, e.g., by using a slack take-up surface to displace the cable on the outbound side of the pulley body of the slack compensating pulley which may generate a tension in the cable along its length and may increase the wrap angle of the cable around the pulley body. The amount of displacement applied to the cable by the slack take-up surface (and therefore the amount of slack removed from the cable) may be a function of the rotation of the pulley body. In particular, the slack removing displacement applied by the slack take-up surface to the cable may be a function of the rotation of the slack take-up surface and/or a support such as a disk, ring, arm, etc. to which the slack take-up surface is attached.

For example, described herein are methods of removing slack from a cable of a transmission system, the method comprising rotating a slack-compensating pulley about an axis of rotation in a first direction of rotation so that a cable held on a cable track along a body of the slack-compensating pulley is drawn in the first direction of rotation, wherein rotating the slack-compensating pulley in the direction of rotation rotates a first slack take-up surface connected to the body of the slack-compensating pulley about the axis of rotation to drive the first slack take-up surface against a first length of the cable to remove slack from the first length of cable.

As mentioned above, slack may be removed from different lengths of cable operated on by a pulley body. The lengths of cable may be parts of a single cable, or parts of different cables. For example, a method of removing slack from a cable of a transmission system may include: rotating a slack-compensating pulley clockwise about an axis of rotation through a rotation point so that a cable on a cable track along an outer surface of the pulley body of the slack-compensating pulley is drawn clockwise, wherein rotating the slack-compensating pulley clockwise rotates a first slack take-up surface connected to the body of the slack-compensating pulley about the axis of rotation to drive the first slack take-up surface against a first length of the cable to remove slack from the first length of cable; and rotating the slack-compensating pulley counterclockwise so that the cable held on a cable track along a body of the slack-compensating pulley is drawn counterclockwise, wherein rotating the slack-compensating pulley counterclockwise rotates a second slack take-up surface connected to the body of the slack-compensating pulley about the axis of rotation to drive the second slack take-up surface against a second length of the cable to remove slack from the second length of cable.

An of the methods described herein may be methods of removing slack from a cable of a transmission system using a slack-compensating pulley having a pulley body, a support extending from the pulley body, and a slack take-up surface on the support, wherein a cable travels along an outer surface of the pulley body. For example, a method may include: rotating the slack-compensating pulley about an axis of rotation in a first direction so that the slack take-up surface rotates with the pulley body about the axis of rotation in the first direction and drives the slack take-up surface against a first portion of the cable extending off of the pulley body to deflect the first portion of the cable so that a path taken by the first port of the cable as it extends off of the pulley body is longer; and rotating the slack-compensating pulley about the axis of rotation in a second direction, so that the slack take-up surface rotates with the pulley body about the axis of rotation in the second direction and withdraws the slack take-up surface away from the first portion of the cable to shorten a path taken by the first portion of cable as it extends off of the pulley body.

Rotating the slack-compensating pulley in the second direction may comprise rotating a second slack take-up surface with the pulley body and driving the second slack take-up surface against a second cable length on a second side of the pulley body and deflecting the second cable length from a second cable path to lengthen the path taken by the second cable length and reduce slack in the second cable length.

In general, any of the methods described herein for removing slack from a cable with a slack-compensating pulley may be used as part of a method for actuating any cable-driven such as a laparoscope or other minimal access tool, a cable or tendon-driven endoscope, or the like. For example, any of the methods described herein may be used to actuate an end effector such as a multi-link end effector joint in response to rotation of the slack-compensating pulley.

A method of removing slack from a cable of a transmission system using a slack-compensating pulley having a pulley body, a support extending from the pulley body, a first slack take-up surface on the support and a second slack take-up surface on the support, wherein a cable travels along an outer surface of the pulley body, may include: rotating the slack-compensating pulley about an axis of rotation in a clockwise direction so that the first slack take-up surface rotates with the pulley body about the axis of rotation in the clockwise direction and drives the first slack take-up surface against a first length of the cable and deflects the first length of cable length to lengthen a cable path taken by the first length of cable off of the pulley body, reducing slack; and rotating the slack-compensating pulley about the axis of rotation in a counterclockwise direction so that the second slack take-up surface rotates with the pulley body about the axis of rotation in the counterclockwise direction and drives the second slack take-up surface against a second length of cable deflects the second length of cable to lengthen a cable path taken by the second length of cable off of the pulley body, reducing slack.

In any of the apparatuses and method described, the slack-compensating pulley may be placed in a neutral position before, during, or after operation of the apparatus. In some variations, the neutral position may be when the first and second slack take-up surfaces are tangential (i.e. barely contacting) to the first length and second length, respectively, of the cable. In some variations the neutral position may include not contacting the cable with a slack take-up surface. For example, the slack-compensating pulley may be held in a neutral position in which neither the first nor the second slack take-up surfaces contact the first length or second length of the cable. These slack take-up surfaces come into contact with the cable only after a finite clockwise or counter-clockwise rotation of the slack-compensating pulley. However, in some variations the neutral position is such that the first and second slack take-up surfaces are engaged with the first length and second length, respectively, of the cable. In other words, in the neutral position, some portion of the first length of cable contacts the first slack take-up surface and/or some portion of the second length of cable contacts the second slack take-up surface, etc.

While the driven and driving pulleys in the examples provided herein are shown to be about the same diameter in the figures, in practice these pulleys can instead be of any two different sizes. Further, although the figures shown herein illustrate slack take-up features on or formed as part of the driving pulley, appropriate slack take-up features may also be included on or integrated into the driven pulley.

Also, while full pulleys are shown in the examples provided herein, in practice the transmission may involve only a fraction of a turn. In such a scenario, the pulley may look like a pie slice rather than a full circle. The methods and apparatuses described herein are particularly relevant to cable driven transmission systems in which the driving pulley rotates by only a fractional turn (i.e. less than 360 degree rotation, less than 320 degrees, less than 300 degrees, less than 280 degrees, less than 260 degrees, less than 240 degrees, less than 220 degrees, less than 200 degrees, and typically less than 180 degrees).

As described, in any of these variations, the apparatuses and methods may be used as part of a transmission system for driving a multi-link end effector joint. Thus, the apparatus may include a multi-link end effector joint, and any of the methods may include articulating a multi-link end effector joint in response to the rotation of the slack-compensating pulley.

Any of the slack-compensating pulleys or slack-compensating transmissions described herein may be used as part of a minimal access tool. A minimal access tool typically includes an input mechanism or control, such as a handle, pedal, etc., having a motion input (e.g., input joint) and a cable transmission for transmitting the motion input from the control to an end effector. Examples of minimal access tools may include, but are not limited to, those shown in U.S. Pat. No. 8,668,702, incorporated by reference in its entirety.

For example, any of the slack-compensating pulleys described herein may be coupled to an input, such as an input joint, to translate an input movement into an actuation of the pulley. A slack-compensating pulley may be coupled to an input joint so that the slack-compensating pulley is rotated about its axis of rotation based on the input motion of the input joint.

A minimal access tool having a slack-compensating transmission may include: a handle; a tool shaft having a proximal end and a distal end, the proximal end of the tool shaft linked to the handle; a transmission extending along the tool shaft, the transmission comprising a cable; an input joint connected to the handle to receive a rotational input from a user's hand; a slack-compensating pulley coupled to the input joint, the slack-compensating pulley comprising: a pulley body; a cable track along a surface of the pulley body on which the cable wraps with a wrap angle; a support extending from the pulley body; and a slack take-up surface on the support, wherein the slack take-up surface is positioned radially further outward than a nearest region of the surface of the pulley body so that the cable passes between the pulley body and the slack take-up surface, wherein the support and slack take-up surface rotate with the pulley body to remove and/or reduce slack in the cable when the pulley body is rotated in a first direction by increasing the wrap angle of the cable on the pulley body; and an end effector at the distal end of the tool shaft, wherein the cable is coupled to the end effector.

The slack-compensating pulley may further include a second slack take-up surface, wherein the second slack take-up surface is positioned radially further outward than a nearest region of the surface of the pulley body so that the cable passes between the pulley body and the slack take-up surface, wherein the second slack take-up surface rotates with the pulley body to remove and/or reduce slack in a second length of cable when the pulley body is rotated in a second direction. For example, the slack-compensating pulley may also include a second slack take-up surface on the support, wherein a second length of the cable extends between the pulley body and the second slack take-up surface, wherein the support and second slack take-up surface rotate with the pulley body to remove and/or reduce slack in a second length of cable when the pulley body is rotated in a second direction.

The cable may have a first cable length extending in a first cable path that is tangent to the surface of the pulley body on a first side of the pulley body, wherein when the slack take-up surface rotates with the pulley body about an axis of rotation in the first direction, the slack take-up surface is driven onto the first cable length on the first side of the pulley body and deflects the first cable length from the first cable path into a longer cable path, and when the pulley body is rotated in the axis of rotation in a second direction, the slack take-up surface is withdrawn away from the first cable length on the first side of the pulley body to shorten the cable path.

For example, a minimal access tool may include: a handle; a tool shaft having a proximal end and a distal end, the proximal end of the tool shaft linked to the handle; a transmission extending along the tool shaft, the transmission comprising a cable; an input joint connected to the handle to receive a rotational input from a user's hand; a slack-compensating pulley coupled to the input joint, the slack-compensating pulley comprising: a pulley body having an axis of rotation, wherein the cable is wrapped on an outer surface of the pulley body so that a first cable length extends in a first cable path that is tangent to the outer surface of the pulley body on a first side of the pulley body; a support extending from the pulley body; and a slack take-up surface on the support, wherein the slack take-up surface rotates with the pulley body so that when the pulley body is rotated about the axis of rotation in a first direction, the slack take-up surface is driven onto the first cable length on the first side of the pulley body and deflects the first cable length from the first cable path to remove slack; and an end effector at the distal end of the tool shaft, wherein the cable is coupled to the end effector.

A minimal access tool may include: a handle; a tool shaft having a proximal end and a distal end, the proximal end of the tool shaft linked to the handle; a transmission extending along the tool shaft, the transmission comprising a cable; an input joint connected to the handle to receive a rotational input from a user's hand; a slack-compensating pulley coupled to the input joint, wherein slack-compensating pulley comprises a pulley body and a slack take-up surface that rotates with the pulley body, wherein the cable wraps around at least a portion of the pulley body at a wrap angle, the cable extending between the pulley body and the slack take-up surface, so that when the pulley body is rotated in a first direction, the slack take-up surface is driven onto the cable to remove slack from the cable by lengthening a cable path taken by the cable off of the pulley body, increasing the wrap angle; and an end effector at the distal end of the tool shaft, wherein the cable is coupled to the end effector.

In general, a handle is just one type of input controls that may be used to provide motion input (e.g., rotational input) to actuate a minimal access tool. As mentioned above, other inputs may be used, including petals and inputs that track motion of other body joints (knees, arms, heads, feet, etc.).

In any of the minimal access tools described herein the, end effector comprise a multi-link end effector. In general, the end effector of a minimal access tool may be separated from the input control (e.g., handle) by a shaft, which may be referred to herein as a tool shaft. The shaft typically extends the reach of the tool. For example, the shaft may be an elongate member extending distally from the handle. The tool shaft may be directly or indirectly linked (e.g., coupled) to the handle. For example, the handle may be indirectly linked to the tool shaft through a frame that allows motion of the handle relative to the frame. The relative motion may be used as the motion input and provided to an input joint for transmission to the end effector.

The end effector may be any effector that can be actuated by the transmission cable. For example, the end effector may include a multi-link end effector joint with or without an additional manipulator (e.g., clamp, pincher, etc.). The end effector may be a grip, a scissor, a screw, etc.

Multi-link, snake-style end effector joints may be used in a variety of applications where wrist-like articulation at the end of a tool or instrument is needed. The wrist-like articulation comprises one or two wrist-like rotations (e.g. pitch and yaw), which provide dexterity at the tool end effector. In all of these cases, the traditional multi-link end effector joint driven by a simple pulley via cables results in a sub-optimal transmission. The driving pulley may be rotated manually or using motors. The transmission in such a case is not truly kinematic in the sense that the end effector rotation is not uniquely determined by the rotation of the driving pulley. In a rotated configuration, the end effector is stiff only in one direction and remains compliant or sloppy in the other direction even when the driving pulley is held fixed. This arises from the geometry or kinematics of a multi-link end effector construction, where upon the driving pulley rotation, the transmission cable drawn in one side is less than the cable released on the other side of the closed transmission. The slack-compensating (also referred to as slack-compensation) features associated with the driving pulley that are described herein may overcome this challenge and make any cable transmission system, including multi-link snake-style end effectors, considerably more effective. These slack-compensating pulleys may be referred to herein as slack-compensating pulleys or tensioning pulleys.

Also described herein are methods of tensioning a cable of a transmission system (including, but not limited to a kinematic transmission system). In general, these methods may use any of the pulleys described herein to compensate for slack in the transmission, and particularly by reducing slack in one or more cables.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

In FIG. 1A, the pulley is shown in its neutral position, before rotation and in FIG. 1B the pulley is shown after counter-clockwise rotation.

FIG. 3A shows the apparatus in a neutral position, and FIG. 3B shows the apparatus being rotated CCW (e.g., 30 degrees). In this example, the slack take-up feature (e.g., each slack take-up surface) has a sliding surface (e.g., a low-friction surface) where it contacts the cable.

In FIG. 4A, the apparatus is in a neutral position, while in FIG. 4B the apparatus is in a rotated configuration (after rotation). In this example, the slack take-up surface includes rolling surface(s) that may reduce friction between the cable and the slack take-up surface.

In FIG. 5A, the apparatus is in a neutral position, while in FIG. 5B the apparatus is in a rotated configuration (after rotation). The slack take-up feature (e.g., support and slack take-up surface) in this variation may include a loading bias, as shown schematically by the spring elements.

FIG. 9A shows the bendable member in an unbent configuration and FIG. 9B shows the bendable member in a bent configuration.

FIG. 12A shows the end effector unbent, with the arms of the pulley in a neutral position, while FIG. 12B shows the end effector bent and one of the pulley arms applying displacement to the cable to remove slack from one of the cables.

FIGS. 16A and 16B illustrate slack in a pulley transmission system.

FIGS. 17A and 17B illustrate the generation of slack in a cable based transmission system such as those (both kinematic and non-kinematic or elastic) described herein.

FIG. 23A illustrates an example of an apparatus having a supports (arms), each support having multiple slack take-up surfaces for applying force against a length of cable to lengthen the path of the length of cable and to remove slack from the length of cable as the apparatus is rotated along with the pulley body to which it is attached. The apparatus and driving pulley are shown in a neutral position in FIG. 23A. FIG. 23B shows the apparatus applying a displacement against a length of cable after the pulley body has been rotated counterclockwise.

FIGS. 24A and 24B show one example of a minimal access tool having a slack-compensating transmission including a handle, an end effector, a tool shaft, and a transmission including a cable and a slack-compensating pulley. FIG. 24A shows the minimal access tool prior to articulation and FIG. 24B shows the minimal access tool after articulation.

DETAILED DESCRIPTION

In general, described herein are slack compensating apparatuses for cable transmission systems, slack compensating pulleys, device (including in particular minimal access surgical tools) including a slack compensating transmission, and methods of operating them. In general, a slack-compensating pulley may have a pulley body with one or more (e.g., two) supports extending beyond the pulley body. The support(s) may include one or more slack take-up surfaces on them. The pulley body, support(s) and slack take-up surface(s) are coupled so that they rotate together about an axis of rotation, and rotation of the apparatus in a first direction will drive at least one of the slack take-up surfaces against a cable wound on the pulley body to reduce or remove slack from a portion of the cable leaving the pulley body. Driving the slack take-up surface against the cable increases the path length taken by the portion of the cable leaving the pulley body and also increases the wrap angle of the cable on the pulley body, reducing slack in the cable. Any of the slack-compensating apparatuses described herein may be used with or may form part of a cable-based transmission system that may have slack due to either geometric/kinematic reasons (e.g. in case of driving a multi-link end-effector joint) or due to elastic reasons (e.g. compliance of cable and/or other transmission elements).

Slack may result in a transmission system due to poor initial tensioning, assembly imperfection, and/or cable elasticity and wear. In addition, slack may result from the geometry or kinematics of the transmission system. The mathematical derivation further below illustrates how slack may be dictated by the geometry of the design and may be referred to herein as "geometric" or "kinematic" slack.

Figures 1A, 1B:
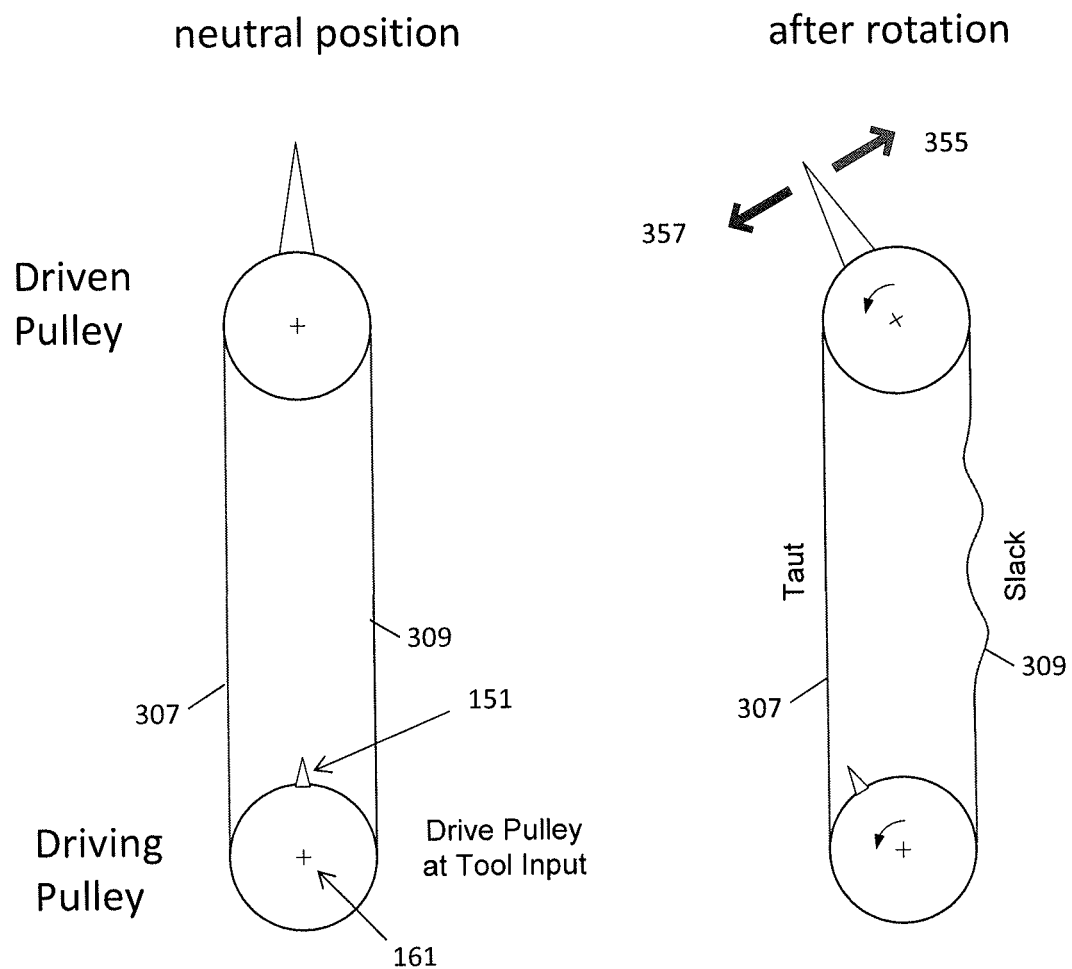
FIGS. 1A and 1B illustrate one example of a cable-driven transmission system including a driving pulley, a driven pulley, and a cable.
Figures 2A, 2B:
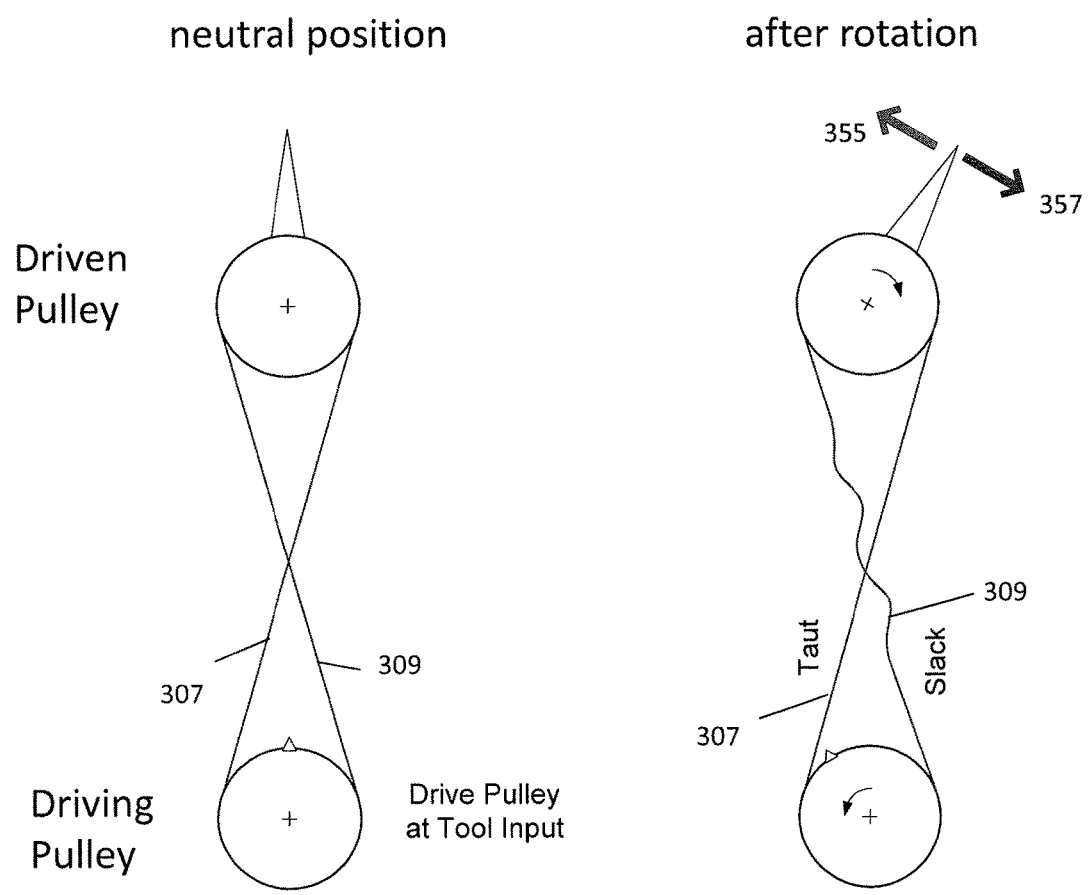
FIGS. 2A and 2B shows another example of a cable driven transmission system both before rotation (FIG. 2A) and after rotation (FIG. 2B). As in the example shown in FIGS. 1A and 1B, elasticity (e.g., stretching) of the cable may lead to the development of slack.

FIGS. 1A and 1B illustrate the generation of slack in a two-pulley transmissions system, including a driven pulley and a driving pulley connected by two lengths of cable 307, 309 (which may be formed of different regions of a single cable or may be two separate cables). In FIG. 1A, the system is in a neutral position, with the driving pulley shown before articulation. There is no tension or some nominal pre-tension on both cables. In FIG. 1B, the drive (or driving) pulley is rotated (e.g., approximately 30 degrees) counterclockwise, pulling one cable region 307 taut, while generating slack in the other cable region 309. This may be because of the elastic nature of the cable. Similarly, FIGS. 2A and 2B illustrate a transmission system in which the cables are not parallel but follow different paths between the components of the transmission system (in this example a driving pulley and a driven pulley). Rotation of the driving pulley counterclockwise rotates the driven pulley clockwise, but results in slack on the outgoing cable 309 while the incoming cable 307 is pulled taut. This may be because of the elastic nature of the cable.

A simplified illustration is shown in FIGS. 16A and 16B, showing the development of slack in a simple transmission system having a pair of pulleys connected by a cable; these pulleys are adjacent and are scaled by a cable without any other interruptions. In FIG. 16A, the cable 1601 is shown having a nominal cable path, which is the shortest distance between the points of tangency between the two pulleys. During operation of the pulleys, however, the actual length 1603 of the cable may diverge from this nominal path length, as shown in FIG. 16B. In this example, the actual length 1603 of the cable between the pulleys is greater than the nominal path length of cable 1601, e.g., due to kinematic or elastic reasons. The difference between the actual length and the shortest possible length (i.e., the nominal path) is the slack. This slack can be measured. The slack may depend on many factors in the transmission system: the cable, the pulleys, their mounting, the compliance or rigidity of this mounting, the path that the cable is routed through, and the overall configuration of the system that these pulleys are a part of. Therefore, predicting the exact amount of slack may be tricky, however for a given system, the amount of slack may be measured or determined empirically. In addition, the amount of compensation for slack provided by a slack take-up system may also be determined directly or indirectly, and the reduction or removal of slack may be confirmed.

FIGS. 17A and 17B illustrate the generation of slack in a portion of a transmission system including a pulley and two lengths of cable (which may be regions of the same cable or may be different cables). FIGS. 17A and 17B show incoming cable 1705 and outgoing cable 1701. In general, slack is typically generated on the outgoing cable side 1701 of the pulley 1703, while the incoming cable is typically taut. This is indicated in FIG. 17A for clockwise rotation and in FIG. 17B for counterclockwise rotation.

Figure 9A:
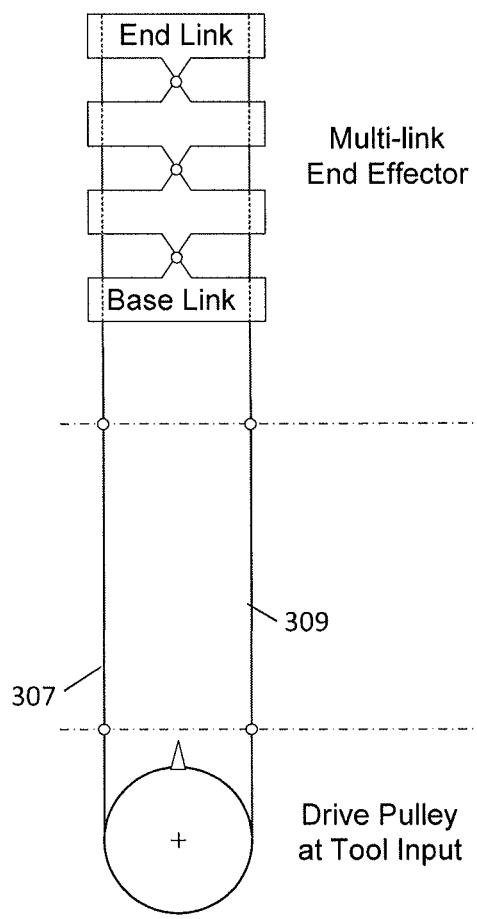
FIGS. 9A and 9B illustrate another variation of an exemplary controllably bendable member having a single rotational direction that is articulated by a driving pulley via a pair of cables.
Figure 9B:
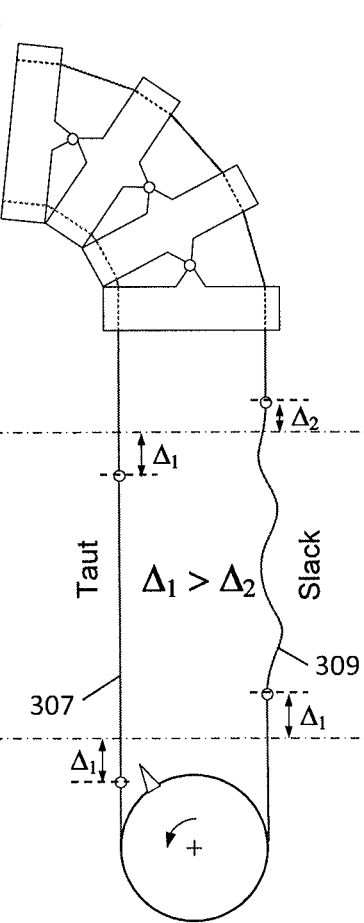

In a transmission system including multiple, connected links, when a large number of links are used to achieve a large range of rotational motion at the end effector, the amount of slack in the cable (shown in FIGS. 9A and 9B on the right hand side cable) may become problematic. This slack may produce several problems in terms of performance of the end effector. For example, ideally, for a transmission system to be kinematic, a fixed rotation or displacement at the input should completely determine the displacement or rotation of the output. In more practical terms, this ensures large holding stiffness and minimal backlash in the transmission, which are generally desirable and often necessary for remote control of articulated end effectors. This provides the ability to push the end effector against objects in its surroundings to carry out desired tasks. Additionally, a kinematic transmission may ensure that forces exerted by the end effector on such objects (and vice versa) are transmitted back to the pulley and ultimately to the driver of the pulley. If this driver is a person, then these transmitted forces provide haptic feedback. The cable slack described above may render the transmission non-kinematic. As noted earlier, this slack is above and beyond any that might arise due to cable stretch, wear, and assembly tolerances. As shown in FIGS. 9A and 9B, in the condition where the pulley is rotated CCW and the end effector joint is rotated towards the left, when an external force corresponding to the upper arrow 356 is applied at the end effector joint, it is resisted adequately by the left hand side cable, which is taut. This leads to good stiffness and little backlash in that direction. However, if an external force at the end effector joint is applied in the direction of the lower arrow 358, then because of the slack in the right hand side cable, the end effector presents poor holding stiffness and finite backlash, both of which are highly detrimental to the end effector articulation performance. This assumes that the links in the multi-link end-effector joint have not yet physically contacted each other.

Figure 10:
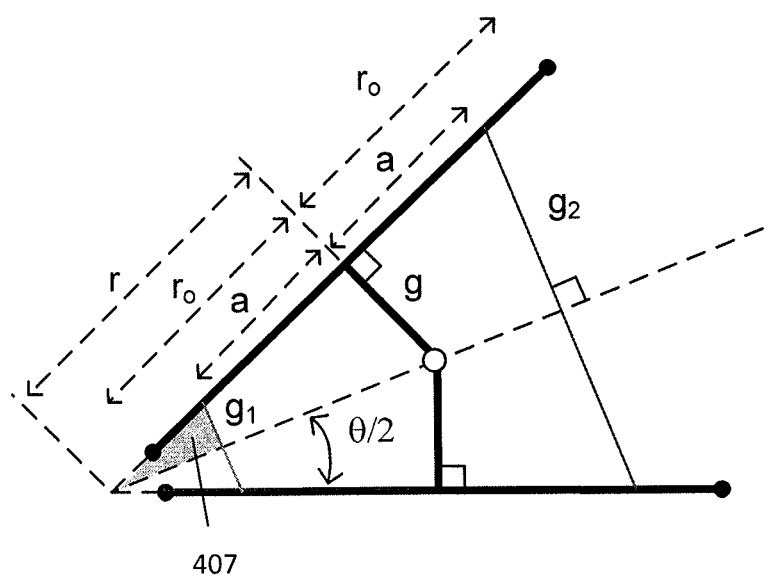
FIG. 10 illustrates the geometry of the relative motion between two consecutive links associated cable kinematics.

As mentioned earlier, the kinematic slack generated may be inherent to the geometry of the multi-link end effector, and may be described mathematically. Referring to FIG. 10, assume a rotation of $\theta$ between two consecutive links. Upon this rotation, the ends of the two links come close to each other on the left hand side, as seen in FIG. 10. The limit to this motion may correspond to the event when the two ends touch each other. For that condition:

$$r = r_0$$

$$\theta = \theta_0 \quad (1)$$

However, this may be examined as a generic configuration, rather than the above limiting case. For any generic rotation of $\theta$ less than $\theta_0$:

$$\tan\left(\frac{\theta}{2}\right) = \frac{g}{r} \quad (2)$$

From the triangle 407:

$$\sin\left(\frac{\theta}{2}\right) = \frac{g_1}{r-a} \quad (3)$$

From equations (2) and (3):

$$\cos\left(\frac{\theta}{2}\right) = \frac{g_1}{g} \cdot \frac{r}{r-a} \quad (4)$$

Next, applying the identity $\cos^2 x + \sin^2 x = 1$, equations (3) and (4) yield:

$$\left(\frac{g_1}{r-a}\right)^2 \left[1 + \left(\frac{r}{g}\right)^2\right] = 1 \Rightarrow g_1 = g\frac{(r-a)}{(r^2+g^2)^{1/2}} \quad (5)$$

Following a similar logic:

$$g_2 = g\frac{(r+a)}{(r^2+g^2)^{1/2}} \quad (6)$$

Referring back to FIGS. 9A and 9B, the amount of cable pulled in on the left hand side (307) for one pair of links is equal to:

$$\Delta_1 = 2(g - g_1) = 2g\left[1 - \frac{(r-a)}{(r^2+g^2)^{1/2}}\right] \quad (7)$$

Similarly, the amount of cable released on the right hand side (309) for one pair of links is equal to:

$$\Delta_2 = 2(g_2 - g) = 2g\left[\frac{(r+a)}{(r^2+g^2)^{1/2}} - 1\right] \quad (8)$$

One can next check to see if $\Delta_1$ is equal to $\Delta_2$, by taking the following difference:

$$\Delta_1 - \Delta_2 = 2g\left[1 - \frac{(r-a)}{(r^2+g^2)^{1/2}}\right] - 2g\left[\frac{(r+a)}{(r^2+g^2)^{1/2}} - 1\right]$$

$$= 4g - \frac{4gr}{(r^2+g^2)^{1/2}}$$

$$= 4g\left[1 - \left(1 + \frac{g^2}{r^2}\right)^{-1/2}\right].$$

Thus it is clear that the right hand side of the above equation is never zero, and is in fact always positive, for a finite value of g. The difference between $\Delta_1$ and $\Delta_2$ only goes to zero as g goes to zero. For practical reasons, g generally cannot be zero in a physical embodiment of a multi-link end effector. As a result, one always faces the condition of $\Delta_1 > \Delta_2$, where the difference itself is a function of r and therefore angle $\theta$. This poses considerable challenges (discussed elsewhere) in creating a driving scheme to articulate the end effector.

The same conclusion may be viewed via a slightly different analytical procedure, where one can simplify equations (7) and (8) by making the assumption that $g \ll r$. This reduces these two equations as follows:

$$\frac{\Delta_1}{2g} = \left[1 - \left(1 - \frac{a}{r}\right)\left(1 + \frac{g^2}{r^2}\right)^{-1/2}\right] \quad (9)$$

$$\approx \left[1 - \left(1 - \frac{a}{r}\right)\left(1 - \frac{g^2}{2r^2}\right)\right]$$

$$= \left[1 - \left(1 - \frac{a}{r} - \frac{g^2}{2r^2} + \frac{ag^2}{2r^3}\right)\right]$$

$$= \left(\frac{a}{r} - \frac{ag^2}{2r^3}\right) + \frac{g^2}{2r^2}$$

$$\frac{\Delta_2}{2g} = \left[\left(1 + \frac{a}{r}\right)\left(1 + \frac{g^2}{r^2}\right)^{-1/2} - 1\right] \quad (10)$$

$$\approx \left[\left(1 + \frac{a}{r}\right)\left(1 - \frac{g^2}{2r^2}\right) - 1\right]$$

$$= \left[\left(1 + \frac{a}{r} - \frac{g^2}{2r^2} - \frac{ag^2}{2r^3}\right) - 1\right]$$

$$= \left(\frac{a}{r} - \frac{ag^2}{2r^3}\right) - \frac{g^2}{2r^2}$$

Thus, comparing equations (9) and (10), it is once again clear that the difference between $\Delta_1$ and $\Delta_2$ arises due to the g/r term. Recall from equation (2) that this ratio is also dependent on the rotation angle $\theta$. Thus, the difference between $\Delta_1$ and $\Delta_2$ can be minimized, which also corresponds to minimizing the transmission system challenges, if either g is small or if one is operating at very small angles $\theta$.

The above derivation shows the amount of slack that may result from one link pair. When multiple link pairs are used, the slack may be even greater. Further, with multiple links the slack is no longer deterministic. It can be estimated to lie within a minimum and maximum value, but the exact value is indeterminate. The source of this indeterminacy is the redundant degrees of freedom associated with any multi-link end effector. Consider rotation in one plane (such as FIGS. 9A and 9B). Here, at the input pulley being driven there is one rotation (or, in kinematic terms, one DoF), but at the output there are multiple pivot joints and therefore multiple DoF. This means that one DoF at the input has to drive multiple DoF at the output, which is the basis of kinematic indeterminacy. This means that for any given input rotation of the pulley, the output (e.g., an end effector joint) can take many different equally permissible configurations. The more the number of pivot joints or links in the end effector, the greater is this indeterminacy. This indeterminacy in the configuration of the output joint or end effector joint has many consequences. For example, the amount of kinematic cable slack generated may also be indeterminate and can only be specified within minimum and maximum bounds. For a given final angle "theta" between the end-link and base link, the intermediate links can take any combination of values. For example, if there were 3 links and 2 joints, then for a final angle of theta, the first and second joints can be at 0 and theta, or theta and 0, or theta/2 and theta/2, or any combination as long as the sum is theta. As shown in the mathematical calculations above, the slack generated is a non-linear function of the pivot rotation angle. Therefore, depending on how the overall angle theta gets divided over the two pivots, the slack generated per pivot (i.e. link pair) is different, and the overall slack generated in the multi-link end effector joint is different. This makes it difficult to manage the slack that is generated.

In general, slack may be problematic for a transmission system. For example, in a cable-driven articulating system, including transmission systems such as articulating end effectors, slack may lead to jumping behavior or jerkiness in the end effector. A multi-link end effector joint may become kinked (i.e., take a shape does not represent a continuous curvature), particularly if a compressive axial force is applied at the end effector joint. A large tension in this cable may produce buckling of a multi-link joint that can result in jerkiness of the end effector rotation, which is also due to above explained kinematic indeterminacy.

Figure 11A:
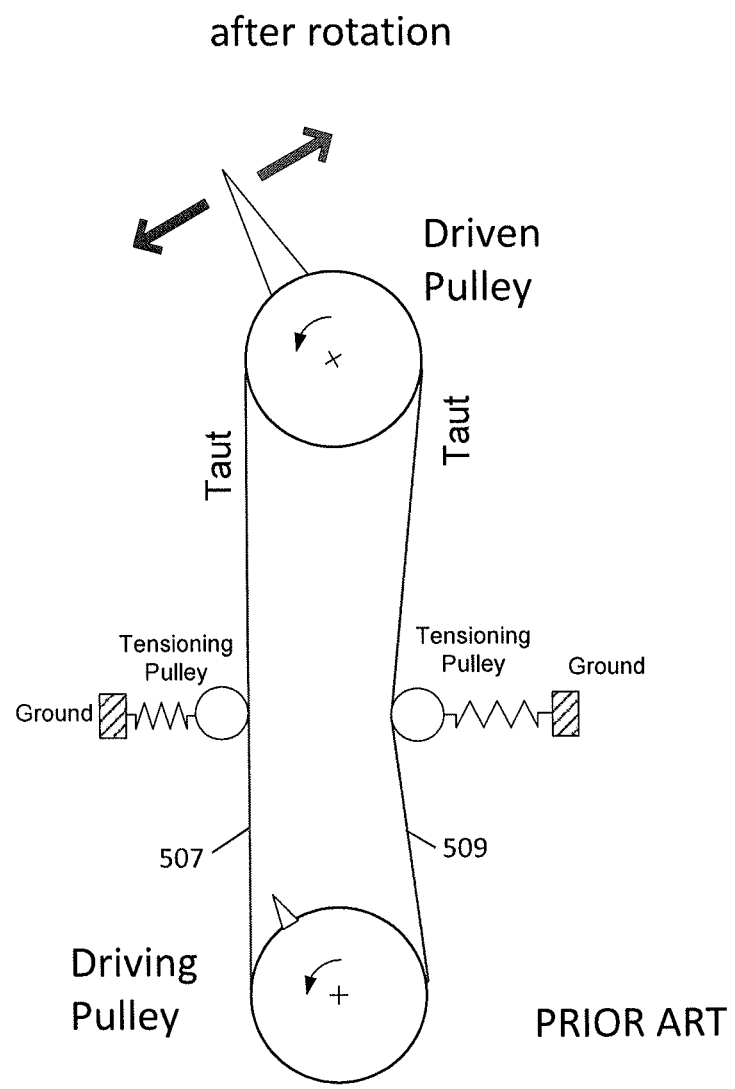
FIG. 11A shows one schematic illustration of a cable tensioning systems using a one or more tensioning pulleys (two are shown) that are mounted via springs to a separate ground (e.g., not connected with the driving or driven pulleys that interface with the cable).
Figure 11B:
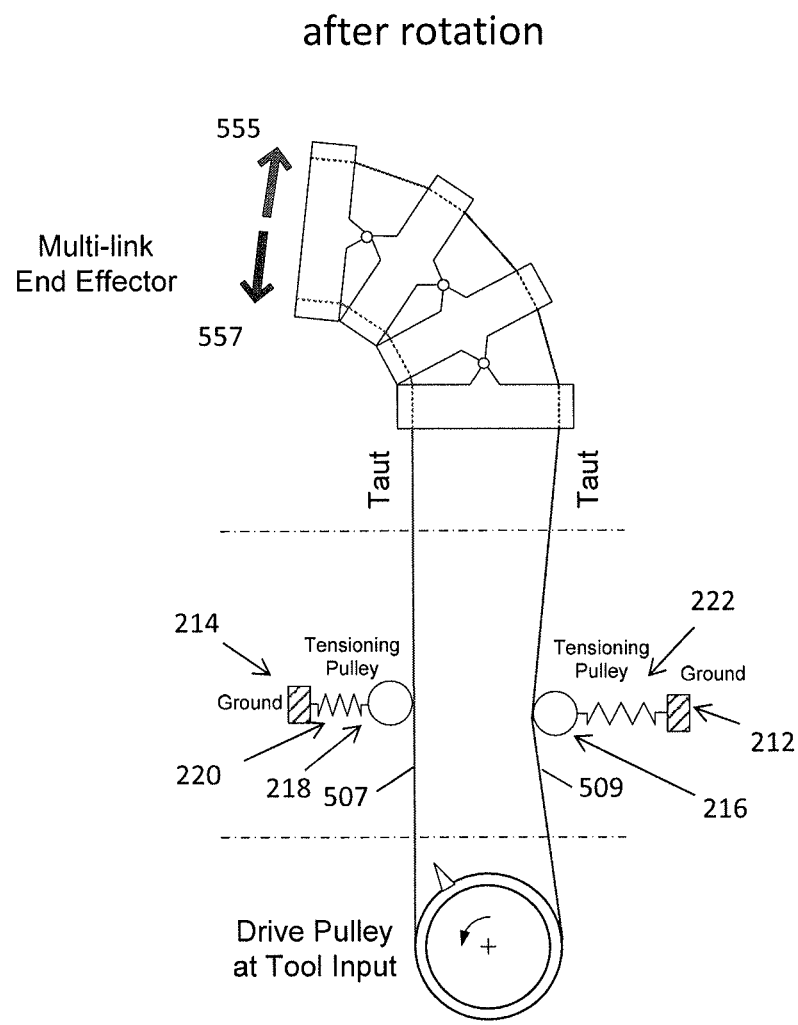
FIG. 11B is a schematic illustration of a cable tensioning system similar to that shown in FIG. 11A for a multi-link end effector joint such as the one shown in FIGS. 9A and 9B.

One solution to the problem of the slack described above is to include spring-loaded tensioning pulleys or other similar features in the transmission system. A typical embodiment is shown in FIGS. 11A and 11B, but other variations are possible. FIGS. 11A and 11B shows schematic illustrations of a cable tensioning systems using a pair of tensioning pulleys 216, 218 that are mounted via spring elements 220, 222 to separate grounds 212, 214 (e.g., not connected with the pulley or pulleys moving the cable). FIG. 11B shows this embodiment coupled to a multi-link end effector joint. In this case, when the end effector is rotated left (input pulley rotated CCW), the spring-mounted pulley on the right hand side cable extends out and picks up the slack generated in the right hand-side cable 509. An analogous situation is repeated when the end effector is rotated to the right (pulley rotated CW). In that case, the left hand-side pulley 507 extends out under the effect of the spring to take up the slack in the left hand side cable. Unfortunately, this category of compensation solutions does not result in a completely kinematic transmission system. For example, any force at the end effector in the direction of the lower arrow 557 is reacted to or countered by the spring on the right hand side. The stiffer one makes this spring, the stiffer the end effector gets in terms of supporting or withstanding external loads. This is highly desirable, but the flip side or tradeoff associated with this choice is that a spring with similar stiffness (because the transmission has to be kept symmetric) is acting on the left side cable as well (which does not need any slack removal in the current configuration). Such a stiff spring adds considerable tension to the left hand side cable, which makes the design of all components more challenging, especially if the overall transmission is being designed for smaller size scales, and increases the effort to rotate (whether manual or via motor) the input pulley to make the end effector rotate. These challenges and design tradeoffs make this particular category of solutions less desirable and effective. In general, in this variation, the spring can be placed at various locations along the transmission and may take various shapes and forms. Other variations of spring-loaded solutions may include a slack pick-up system in-series with the transmission cable (as opposed to, in parallel, as in FIG. 11B). A slack pick-up system may be similar to the self-winding spring-loaded spools used in devices such as measuring tapes. If the spring is too soft, then the advantages of slack pick-up are lost. On the other hand, if the spring is too stiff then it adds considerable loads on various components due to high cable tension and leads to other design challenges.

Figure 12A:
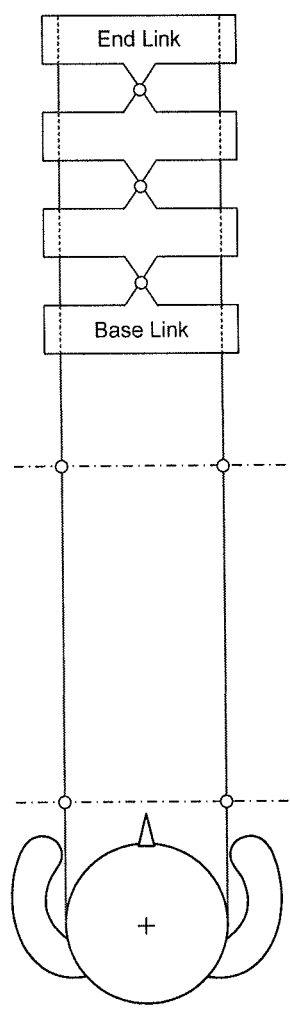
FIGS. 12A and 12B illustrate one variation of a cable tensioning system for a multi-link end effector using a driving pulley having arms or wings that may apply displacement to a cable in some orientations to remove slack from the cables.
Figure 12B:
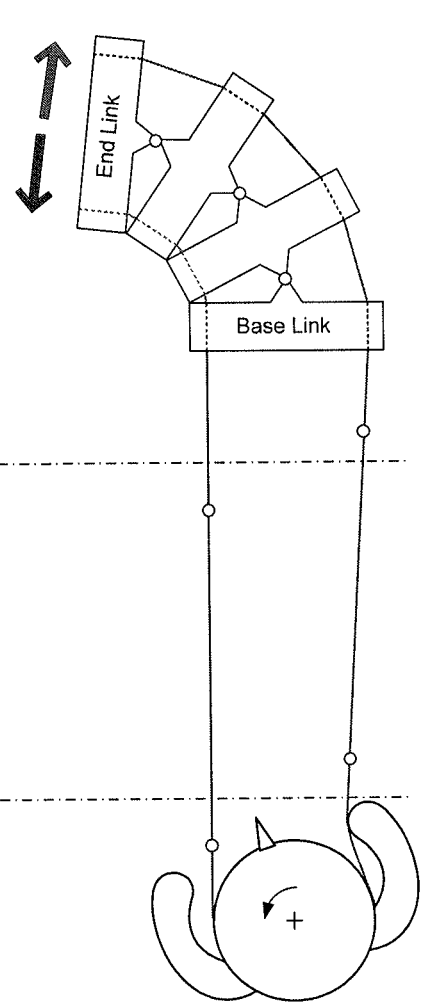

Described herein, and illustrated in FIGS. 3A-3B, 4A-4B, 5A-5C. 6A-6B, 13A-13B, 14A-14B, 15A-15B and 19A-19B, as part of a transmission system including an end effector in FIGS. 12A and 12B are slack-compensating pulleys (also referred to herein as tensioning pulleys) that remove slack from a length of cable by lengthening the path taken by a length of cable being acted upon (e.g., the outgoing cable leaving the pulley), to remove or reduce slack. Thus, the resulting slack-compensating pulleys may include a support (e.g., a generally rigid and/or compliant support, such as an extension, arm, plane, disc, etc.) that pushes against a portion of the cable only on the slack side of the cable transmission arrangement, e.g. only on the outgoing length of cable, and does not affect the taut (incoming length of cable) side. This action is the reverse of a traditional cam action, and a traditional cam action may not be practical in many of the transmission systems described herein.

Figures 3A, 3B:
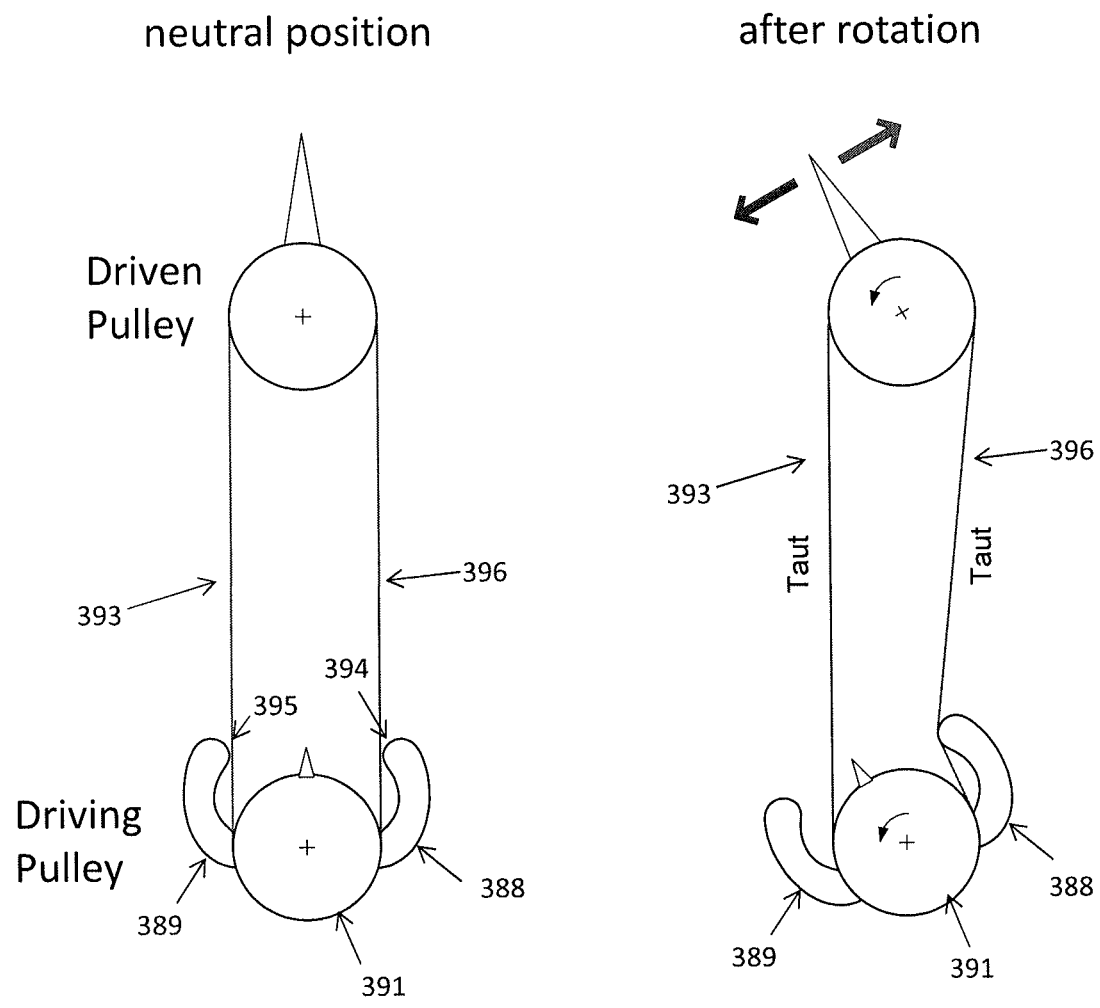
FIGS. 3A and 3B illustrate one variation of an apparatus as described herein, including a pulley body connected with (and/or integrated with) a slack take-up surface comprising a pair of cable contacting surfaces on each of a pair of arms or wings extending from the driving pulley.
Figures 4A, 4B:
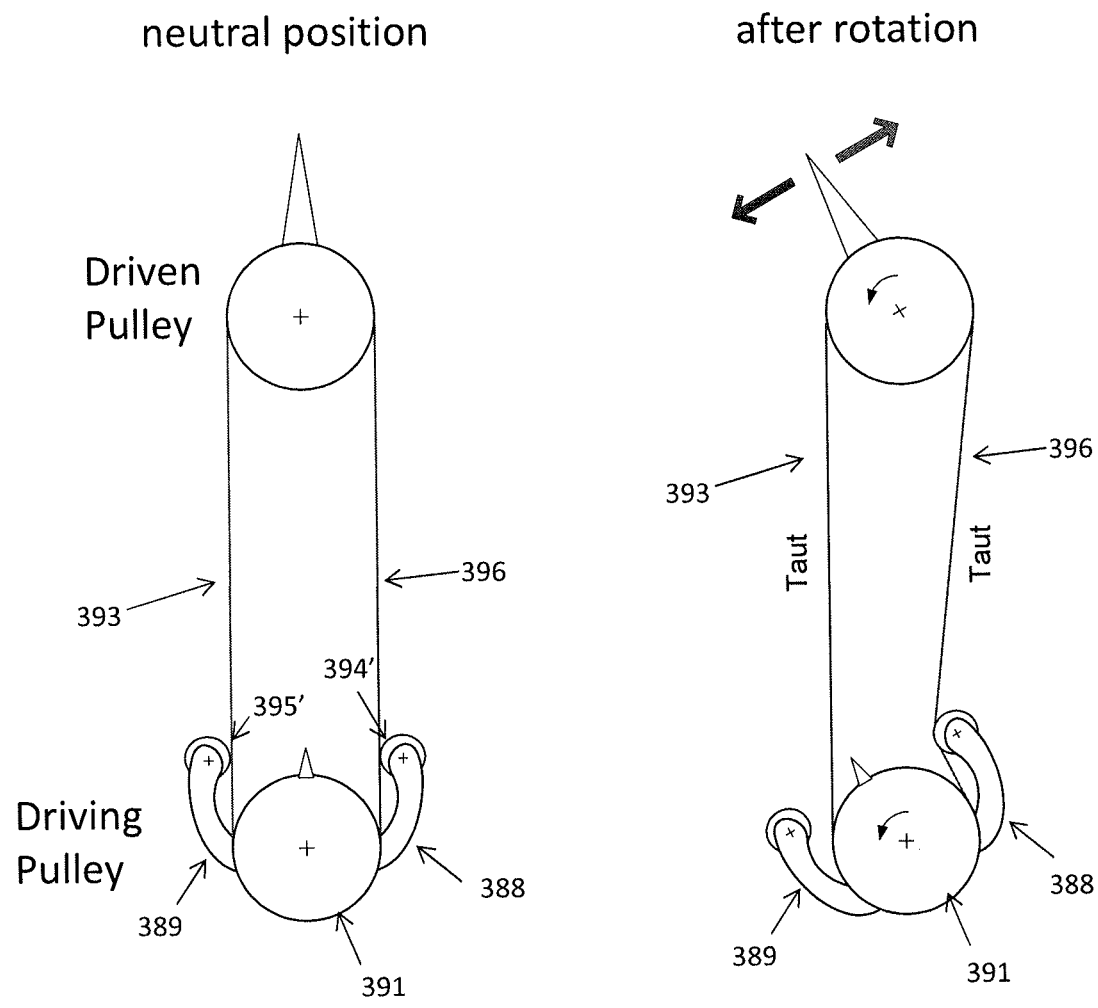
FIGS. 4A and 4B shows another variation of an apparatus including a pulley body connected and/or integrated with a slack take-up surface as described herein, in order to remove a percentage of the slack in the cable.

For example, FIGS. 3A and 3B illustrate a transmission system (or portion of a transmission system) including a slack-compensating pulley. In this example, the slack-compensating pulley is configured as a driving pulley (though it may also be configured a driven pulley, or both the driving and driven pulleys may be slack-compensating pulleys). The slack-compensating pulley includes a pair of support members 388, 389 that are configured as extensions or arms that project from the pulley body and are connected to the pulley body 391 (e.g., behind the pulley body, not shown). Both support members 388, 389, include a slack take-up surface that is configured to contact region of the cable. In FIG. 3A, the slack-compensating pulley is in a neutral position so that the support members and contact regions do not apply do not apply any additional force/tension to the cable regions 393, 396 on either region of cable. In FIG. 3B, the slack-compensating pulley is rotated counterclockwise, and the right side support member rotates with the pulley to drive the slack take-up surface 394 against the outgoing cable 396 so that both the outgoing and incoming cables are taut. FIGS. 4A and 4B illustrate a similar variation, having rollers on the slack take-up surfaces 394' and 395'. These rollers may reduce the friction and/or wear between the cable and the slack take-up surfaces of the slack-compensating pulley.

Although most of the examples (including that as shown in FIGS. 3A-3B and 4A-4B) illustrate examples having a pair of symmetric slack-compensating mechanisms (supports, e.g., arms, and slack take-up surfaces) that are symmetrically arranged about the pulley body, this is not necessary. In any of the apparatuses described herein, the slack-compensating apparatus may include only a single slack-compensating mechanism, such as a support (e.g., arm) and slack take-up surface to rotate with the pulley and provide a displacement against a region of cable to remove slack. In any of the apparatuses described herein, the slack-compensating apparatus may include a pair of non-symmetric slack-compensating mechanisms (supports, e.g., arms, and slack take-up surfaces) that may have different geometries.

Figure 5A:
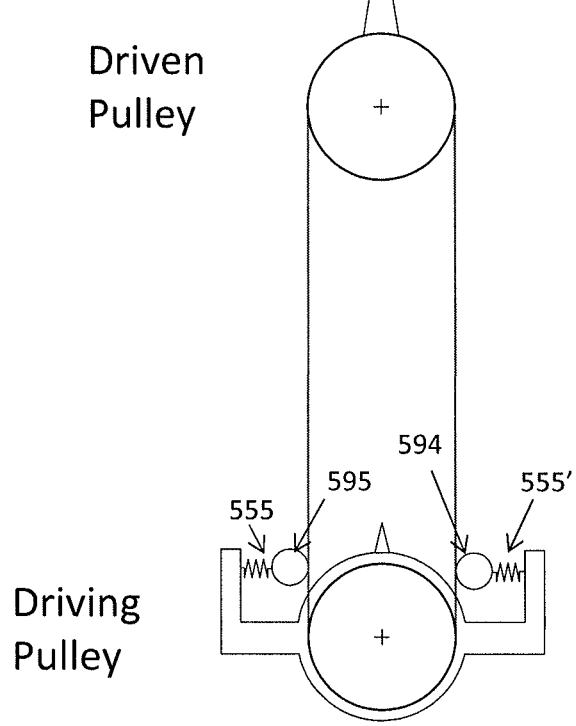
FIGS. 5A and 5B illustrates another variation of an apparatus including a pulley body connected and/or integrated with a slack take-up feature as described herein, in order to remove a percentage of the slack in the cable.
Figure 5B:
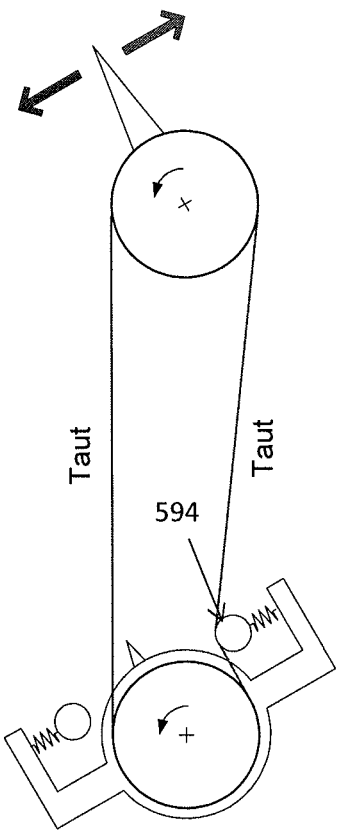
Figures 6A, 6B:
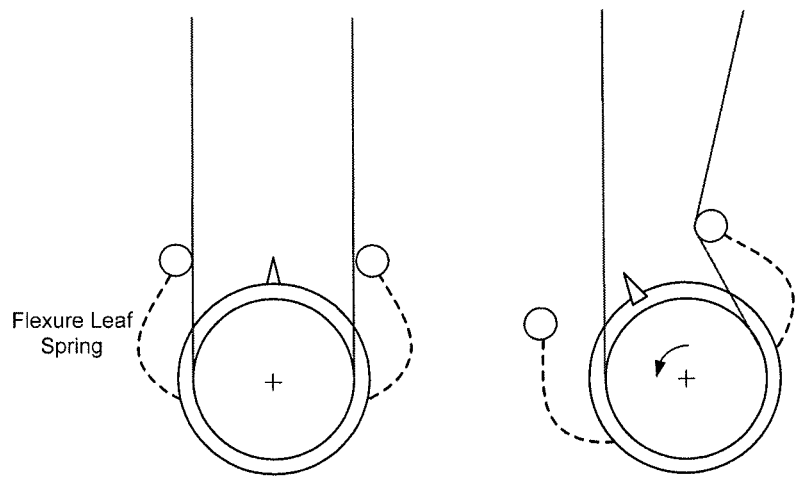
FIGS. 6A and 6B show another variation of an apparatus including a pulley body connected and/or integrated with a pair of arms configured as the slack take-up feature; in this example, the slack take-up feature includes or is formed in part from a flexible material (e.g., forming a leaf-spring like structure).

Any of the slack-compensating members described herein may be configured to apply a variable force on the cable. For example, in some variations, as shown schematically in FIGS. 5A and 5B and 6A-6B, the slack-compensating pulley may include a support member (and/or slack take-up surface) that is elastically connected to rotate with the pulley body. In FIGS. 5A and 5B, the slack-compensating pulley includes a pair of supports configured as arms that extend from the pulley body as described above, however, the arms include (or are configured to act as) a bias or spring element 555, 555' before the slack take-up surfaces 594, 595. Thus, as the slack-compensating pulley is rotated (as shown in FIG. 5B), rotating the support and driving the slack take-up surface 594 against the outgoing length of cable, the force (tensioning force) applied by the contact support 594 may be varied, e.g., reducing or adjusting compensating force/tension against the region of cable, and therefore the friction between the cable and the slack take-up surface 594. Similarly, in FIGS. 6A and 6B, the supports 598 (in this example, support arms) themselves may be elastic, and may act as leaf spring elements.

In FIGS. 12A and 12B, the slack-compensating pulley is integrated into a transmission system including a multi-link end effector. As illustrated in FIGS. 12A and 12B, when a slack-compensating pulley is turned CCW to rotate the end effector towards the left side, because the pulley extensions (arms, wings or loops) are integrated with or connected (e.g., rigidly connected) to the pulley, the left side extension lifts off the cable, without affecting the left hand side cable, which is already taut. However, on the right hand side, where cable slack does get generated, the pulley extension is configured (e.g., by its size and shape) so that it pushes into the cable region on the right hand side by an amount sufficient to pick up the extra kinematic slack that is generated due to the multi-link end effector. An analogous action is repeated when the pulley is rotated the other direction. In this case, the pulley extension (arm, wing, etc.) on the right hand side moves out of the way of the right leg of the cable, and the pulley extension on the left side applies tension to remove the slack that generated on the left hand side cable.

Thus, in FIGS. 12A and 12B and similar embodiments of the slack-compensating pulley, the resulting transmission is kinematic. For given rotation of the driving pulley, the rotation of the driven pulley is completely determined. In other words: the slack was created due to geometry/kinematics and this slack is now taken out due to the geometry/kinematics of the arms extending from the pulley. The end effector provides the desired stiffness against external loads without relying on any springs in the system. Since there is no reliance on springs, there is no need for the tradeoffs associated with springs described above, and now the transmission may be considered kinematic.

The system may be designed so that the support(s), e.g., extensions (arms, wings, etc.), are barely or just touching the cables in the un-rotated (neutral) configuration. In practice, the apparatus may include some initial interference, to ensure that any residual slack at the time of assembly is taken out. Also, this may ensure that the slack elimination scheme can be made more responsive even for small angles of rotation.

Figure 23A:
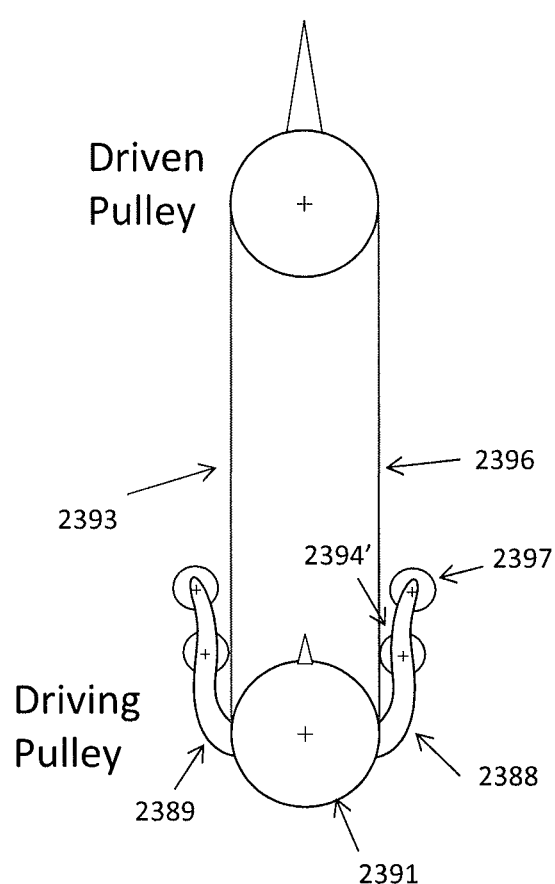
FIGS. 23A and 23B illustrate another example of a slack-compensating apparatus configured to remove slack from a cable-based transmission system.
Figure 23B:
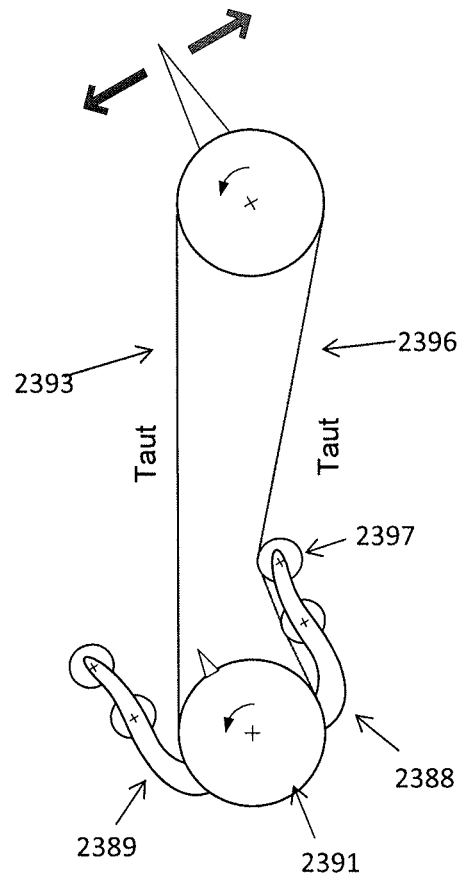

As mentioned above the slack-compensating apparatuses described herein may include more than one slack take-up surface that is arranged to apply a displacement to the same length of cable as the apparatus (including the pulley body) is rotated. For example, FIGS. 23A and 23B illustrate an example of a slack-compensating apparatus having a pulley body and a pair of supports 2388, 2389, (configured as arms), in which each support includes two slack take-up surfaces. In this example, the different slack take-up surfaces may be configured (positioned) so that they engage the cable at different rotational positions. For example, as shown in FIG. 23B, the lower slack take-up surface 2394' may engage with the outgoing cable region 2396 first, while the upper slack take-up surface 2397 engages as the rotation of the cable body increases (upper slack take-up surface 2397'). Alternatively, the multiple slack take-up surfaces may engage with the same region of cable over the same range of rotation. Thus, in general, there can be multiple slack take-up surfaces that engage in an additive manner as one continues to rotate the driving pulley 2391. In FIGS. 23A and 23B, by initially engaging on lower slack take-up surface 2394' (roller) and then later two slack take-up surfaces 2394', 2397' (rollers) on the region of the outgoing cable 2396, the apparatus may initially have a mild slack take-up and a more aggressive slack take-up subsequently. This example is similar to the case, described herein, in which the slack take-up surface provides a non-circular pin/roller (e.g., a cam surface) that engages the cable as the device is rotated.

The size and shape of the support (extensions) may be controlled to provide the appropriate amount of tension on the cables, based on the geometry of the cabling and the pulley body. For example, they may be optimized for transmission performance while taking into consideration other factors in the system such as: clearances at interfaces that produce additional slack (e.g. clearance in the holes in the multiple links through which the transmission cables are routed), assembly tolerances and misalignment, and elasticity (i.e. lack of perfect rigidity along its length) in the cable or other components of the transmission. Mathematical modeling to determine the size and shape of the extensions for given transmission system may be performed to optimize these variables, as illustrated in the example of FIGS. 12A and 12B for a single rotation of the end effector in the plane of the paper, however, it is equally valid for two planes of motion, e.g., for an end effector with two desired rotations, that may be generally orthogonal to each other (e.g. pitch and yaw in FIG. 7). In that situation, two driving pulleys may be used for the two sets of transmission cables. Each pulley may have the extensions (e.g., rigid arms) shown in FIGS. 12A and 12B.

One advantage of the proposed design is that it may leave every other component of a transmission system unchanged. Given all other components and their dimensions, one can simply come up with the right shape and size of the extensions, in general, after the rest of the transmission design has been finalized. That is because of the realization that the slack take-up system only affects the pulley design and generally nothing else. Thus a typical/traditional driving pulley can be simply replaced by a pulley with the proposed extensions.

In general, the supports (arms) 388, 389 shown in FIGS. 12A and 12B may be rigid extensions of the pulley to ensure a kinematic transmission. In practice these extensions may be implemented via a monolithic design, or could be assembled features, or could be embedded/integrated features.

Figures 13A, 13B:
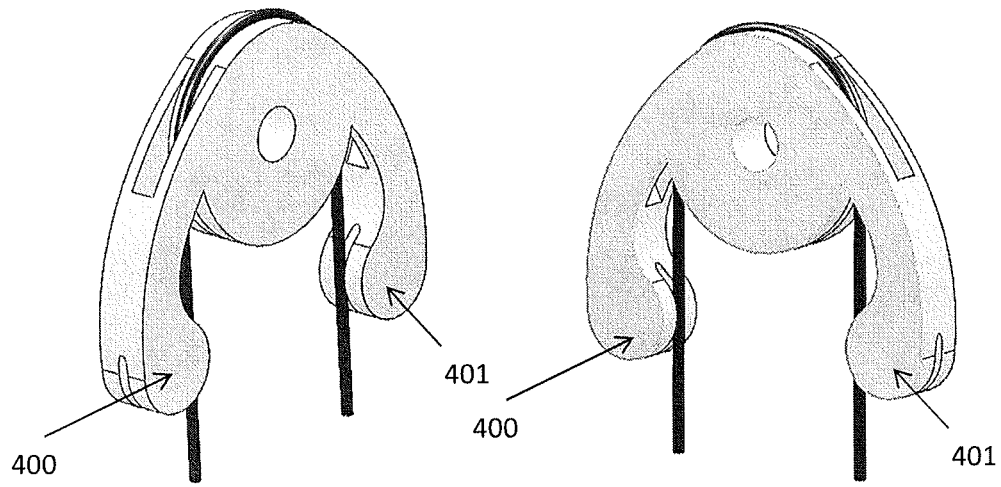
FIGS. 13A and 13B illustrate an example of a slack-compensation driving pulley having tensioning arms, configured as wings, in left and right perspective views, respectively, wherein the slack take-up surface between each arm and respective cable is in the shape of a cam.

The pulley and the support (extension) may be made of different materials or of the same materials. For example, the slack take-up surface of the support (e.g., the portion of the support that contacts the cable) may be cylindrical in shape, or it may have another shape (such as in the case of a cam), or could incorporate a roller, and the roller itself could have spring mounting, as illustrated and described above. Various design embodiments and manufacturing/assembly methods can be used. For example, FIGS. 13A and 13B illustrates another variation of an integrated slack-compensating pulley that may be used as part of a transmission system. In one embodiment, the slack-compensating pulley has flanges 400, 401 that extend beyond the OD of the pulley surface that the cable rides on; the flanges may include drilled holes and a pin or dowel may be extended through the holes.

Figures 14A, 14B:
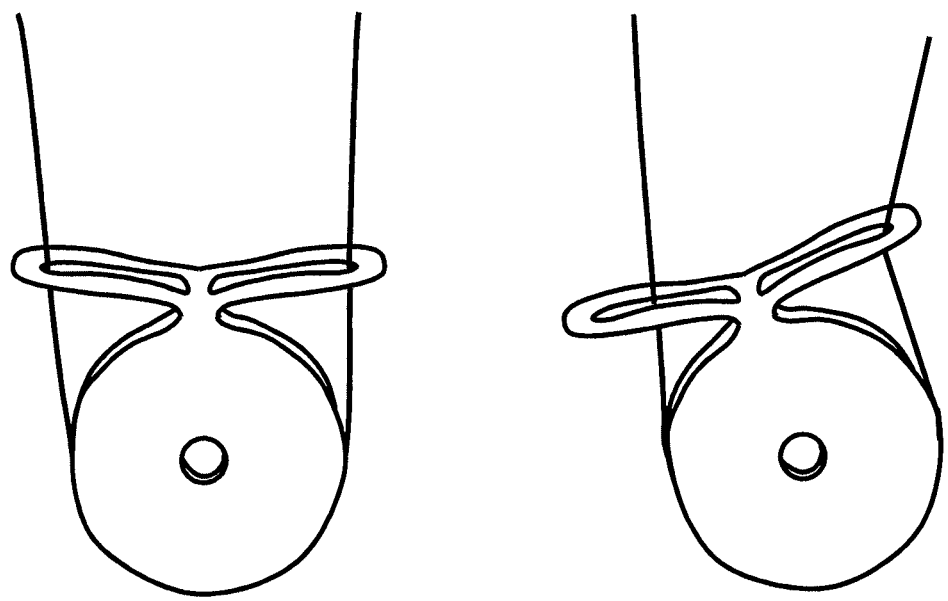
FIGS. 14A and 14B illustrate front perspective views of another example of a pulley having tensioning arms, configured as loops, shown in a neutral position (FIG. 14A) and with the pulley rotated to operate an end effector joint (not shown) and apply displacement via slack take-up surfaces at the loops to remove slack from the cable on the side opposite to the direction of end effector joint bending.

FIGS. 14A and 14B illustrate another variation of a slack-compensating pulley as described herein. In this example, the apparatus is configured to include a pair of supports 388, 389 (extensions), configured as arms or wings having a loop through which the pulley extends. Both arms extend from a common point on the pulley body, however, they may instead extend from different regions (which may be in or out of the plane normal to the axis of rotation). The contact region 394, 395 with the cable legs are within the loops formed by the arms, and rotation of the pulley results in the application of tension and removal of slack, similar to the variation shown above in FIGS. 12A-13B, and illustrated in FIG. 14B.

Although rigid arms (extensions) are shown in FIGS. 12A-13B), in some variations the arms may be compliant (e.g., made of a relatively compliant material, or including a rigid material that is attached to be compliant, e.g., spring-loaded) such as shown in FIGS. 5A-6B.

Figure 15C:
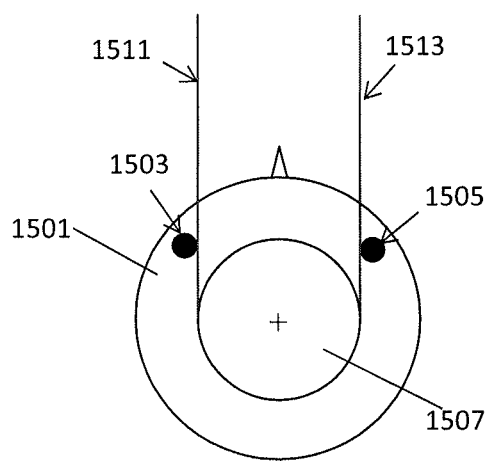
FIGS. 15A and 15B show one variation of a pulley connected and/or integrated with a slack take-up feature, in this variation configured as pair of pins (protrusions) extending from a support (e.g., a boss or plate parallel to, but offset from the plane of the cable on the pulley body) distance beyond the radius of the pulley. A schematic variation of the device in FIGS. 15A and 15B are shown in FIGS. 15C and 15D, respectively.
Figure 15D:
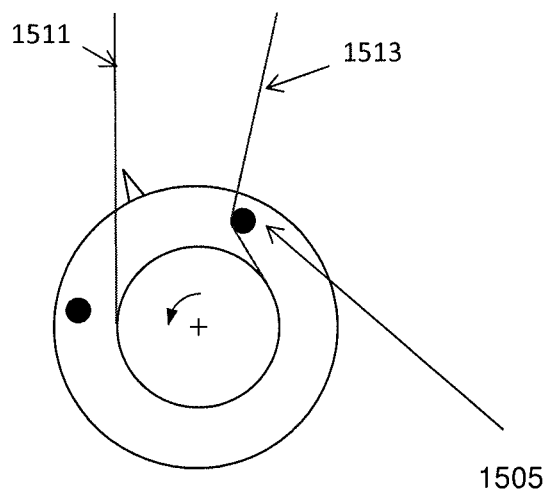
Figure 15A:
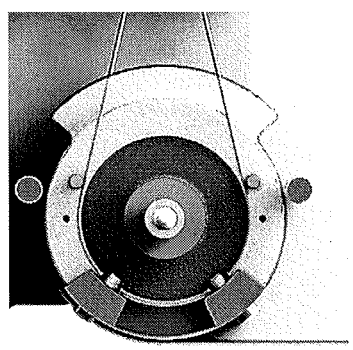
Figure 15B:
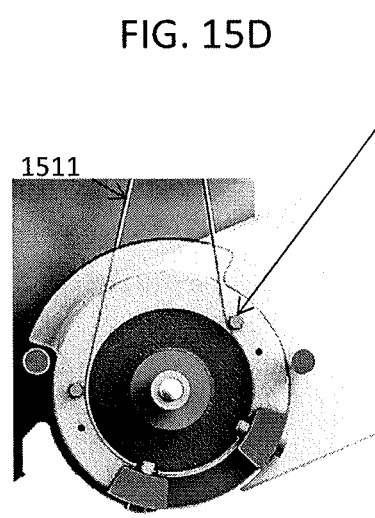

FIGS. 15A-15D illustrate another variation of a slack-compensating pulley in which the support is a disk of material 1501 on one side of the pulley body 1507. The region of cable on the left side in FIGS. 15B and 15D 1511 is taut. Attached to the support (disk or flange) are two nubs (e.g., pins, etc.) 1503, 1505 that provide slack take-up surfaces to apply a tensioning force to compensate for the slack as the pulley is rotated, as shown in FIG. 15B, in which slack on the outgoing length of cable 1513 is compensated by the pin 1505 forming this slack take-up surface. The support may be a full disk (as shown in FIGS. 15A-15D) or a portion of a disk (e.g., just supporting the slack take-up surfaces). The nubs (e.g. pins) may be either assembled into the pulley flange, or may be incorporated integrally with the pulley flange during the latter's fabrication.

Figure 19A:
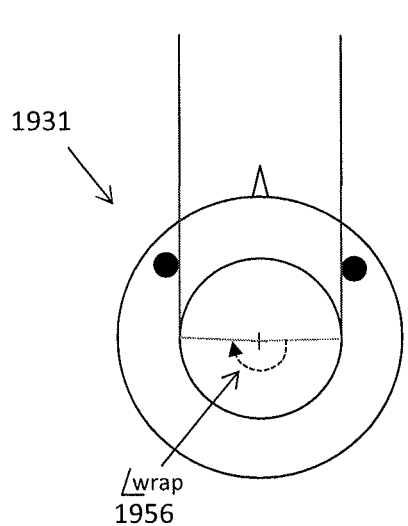
FIGS. 19A and 19B shows another example of an apparatus including a slack-compensation driving pulley having a pulley body and a slack take-up surface integrated or operationally connected with the pulley, wherein the apparatus is configured to reduce slack over a predetermined allowed rotational range (e.g., between −90 and 90 degrees).
Figure 19B:
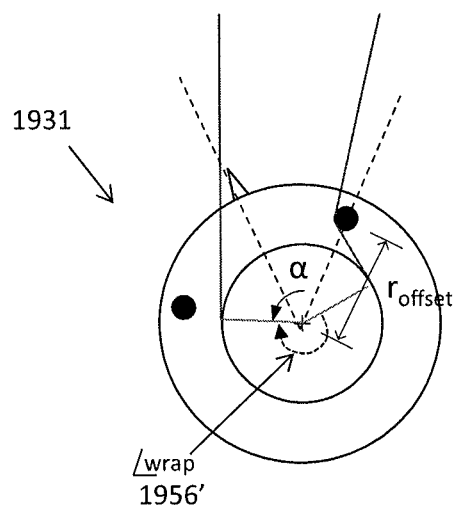
Figure 19C:
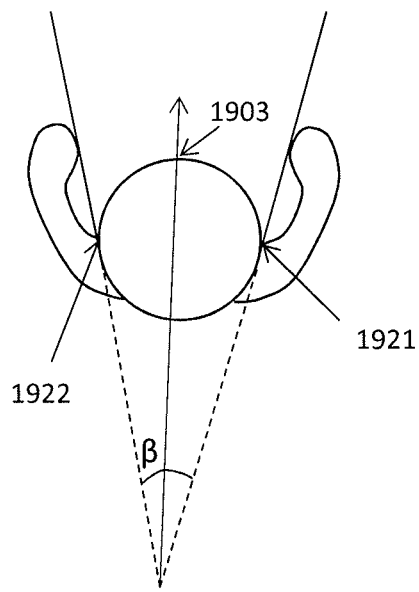
FIGS. 19C-19E illustrate an example of an apparatus including a driving pulley with a slack take-up element including a pair of supports (a pair of arms) and a slack take-up surface on each arm. In these examples the cables (lengths of cable) approach the pulley bodies from different directions, and illustrate the top of the pulley body relative to the position of the cables relative to the pulley body.
Figure 19E:
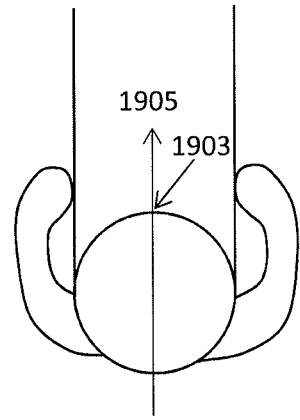
Figure 19D:
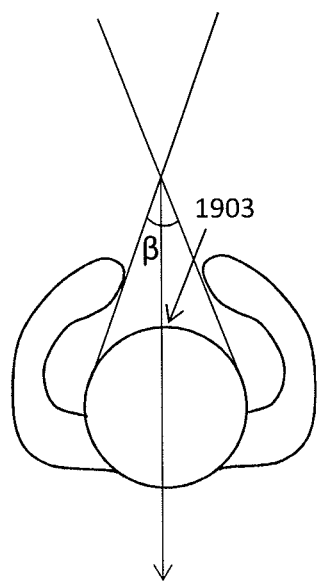

In any of the variations described herein, the position of the slack take-up surfaces may be determined to optimize the slack take-up by the slack-compensating pulley. For example, the amount and type of slack compensation by the slack-compensating pulley may be determined in part (and set) by either or both the radial position of the slack take-up surface, an angle $\alpha$ (e.g. offset from the top of the pulley body, and/or relative to the normative path of the length of cable to be acted on the slack take-up surface), as well as the axial offset from the surface of the pulley body, a distance $r_{offset}$ as illustrated in FIG. 19B, as well as the radius of the slack take-up surface.

Figure 18:
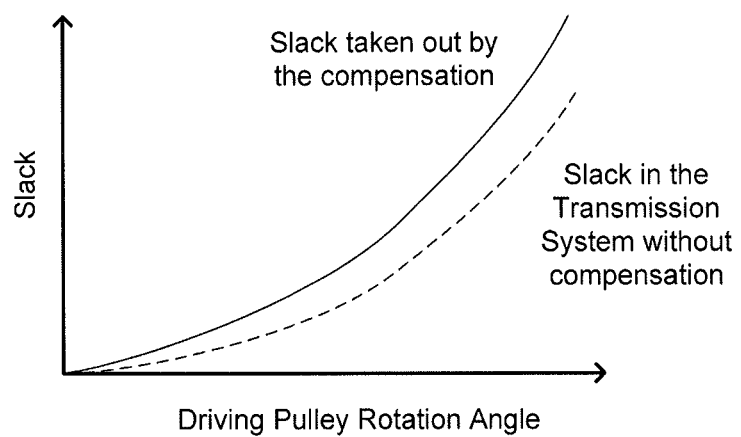
FIG. 18 is a graph showing a mapping of the slack relative to driving pulley rotational angle in an uncompensated transmission system (dashed line) and the slack taken out by the compensation system (solid line). Slack may be compensated using any of the apparatuses or methods described herein.

In general, any of the slack-compensating pulleys described herein may be configured to exactly compensate for slack, overcompensate for slack, undercompensate for slack, or some combination of these. As discussed above, slack may be measured. For example, FIG. 18 illustrates a transmission system with slack (shown by the dashed line). Without compensation, the amount of slack may be determined as a function of the driving pulley rotational angle; generally, the larger the rotation angle, the greater the slack in the outgoing cable region. Any of the systems described herein may be configured to compensate for this slack, including compensating based on the amount of rotation. The slack in the transmission system can be predicted and/or measured. Thus, slack in the system can be known apriori. Although slack exists on the outgoing side of a pulley, this slack is typically referred to as "slack in the system", as there is typically no slack on the incoming side of the pulley (incoming length of cable). When the driving pulley is a nominal position (i.e. zero rotation), there is usually no slack in the system. As the driving pulley starts to rotate that slack increase and can follow any general pattern with increasing rotation, as illustrated by the dashed line in FIG. 18, showing slack in the system in the absence of any slack-compensating elements. In FIG. 18, the solid line is slack taken out by the compensation system. Therefore, the difference between the solid and the dashed lines represents the slack in the compensated system. In FIG. 18, the resulting "slack" will be negative slack (i.e. cable will be stretched) in the compensated system. For example, in some variations, more than 100% slack may be taken up, which means that the apparatus (e.g., the slack compensating apparatus) is stretching the cable. If slack removal is exactly equal to slack generated, then there is no additional tension. But generally, slack take-up may be designed to be greater than slack generated, resulting in a desirable tension buildup in the cable.

Thus, a slack-compensating pulley may be configured to compensate for slack by selecting the distance between center of pulley and center of slack take-up element, $r_{offset}$, and the size as well as shape of the slack take-up element, including the angular position of the cable contracting surface a (e.g., relative to the pulley body and/or cable region to be acted on), and possibly other design parameters. For example, if the slack take-up surface of the slack take up feature is a protrusion (for example, a pin) such as shown in FIGS. 19A-19B or FIGS. 15A-15D, then relevant design parameters may include the distance between the center of the pulley and center of the pin, and the diameter of the cylindrical pin, as well as the angular position of the pin.

The slack take-up feature (e.g., the support and the slack take-up surface) may have any configuration, such as discussed above. For example, the slack take-up surface may be a non-circular surface with varying curvature (i.e. like a cam). In this case, other design parameters may be used, such as the distance between the center of the pulley and some reference point on the slack take-up surface of the slack take-up feature, and then size and shape of the slack take-up feature with respect to this reference point, and/or the angular position of the slack take-up surface.

Once the slack in the transmission system without any compensation is known (either via prediction/modeling or direct measurement), the slack take-up feature may be configured to take out a known amount of slack, which would also be a function of the pulley rotation (e.g., see the solid line in FIG. 19B). In FIG. 19B, the slack-compensating pulley is configured to overcompensate for slack in the system, so that at a given rotation angle, more slack is removed (increasing the path length on the outgoing region of the cable and increasing the wrap angle 1956, 1956'). For example, the slack take-up surface may be positioned further from the outer surface of the pulley body, so that even small rotations of the pulley body result in relatively large rotations of the slack take-up surface.

Figure 20:
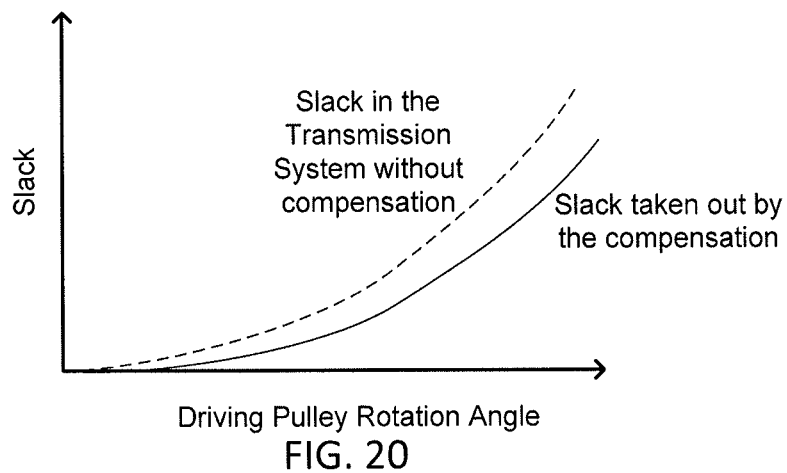
FIG. 20 is another graph showing a mapping of the slack relative to driving pulley rotational angle. The dashed line shows the uncompensated transmission system while the solid line illustrates the slack taken out by the compensation from an apparatus including a pulley and slack take-up element (or integrated pulley with slack take-up element), undercompensating for the known slack in the system.
Figure 21:
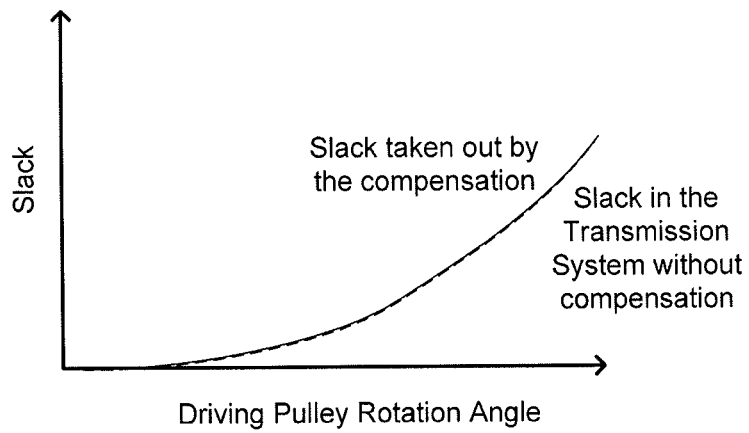
FIG. 21 is a graph showing a mapping of the slack in a system relative to driving pulley rotational angle. In this example, a driving pulley apparatus including a slack take-up element as described herein exactly compensates for the slack in the system over a predetermined allowed rotational range (e.g., between −90 and 90 degrees), as shown by the overlap between the dashed (slack in the transmission without compensation) and solid (slack taken out by the compensation) lines.
Figure 22:
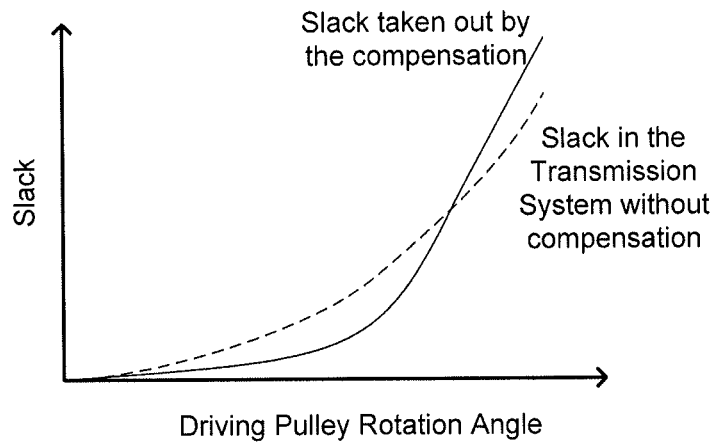
FIG. 22 is another graph showing a mapping of the slack in a system relative to driving pulley rotational angle. In this example, the apparatus including the slack take-up element overcompensates over a portion of the rotation of the driving pulley and undercompensates over another portion of the rotation of the driving pulley, as illustrated by the solid and dashed lines.

Alternatively, FIG. 20 illustrates a system having slack (dashed lines) and a slack-compensating feature configured to undercompensate for this slack (solid line). FIG. 21 shows a system in which the slack (dashed line) is nearly exactly compensated by a slack-compensating feature (solid line). In some variations, as illustrated in FIG. 22, the slack-compensating feature (e.g., slack-compensating pulley) may be configured to under-compensate over certain range of driving pulley rotation and over-compensate over a different range of driving pulley rotation or vice versa. Undercompensation generally reduces frictional resistance in the transmission system, while over-compensation generally increases the stiffness of the transmission system making the driven pulley more responsive to the driving pulley.

Any of the variations described herein may also incorporate a structure at the end effector joint that ensures that any final angle between the end link and base link is uniformly distributed among the link pair/pivot joints. The can be accomplished via, for example, a passive spring either on the inside or outside of the end effector joint. The use of internal or external spring(s) may provide a uniform angular displacement distribution action by virtue of elastic averaging. This may also be accomplished by independently driving the multiple links of the end effector using multiple drivers or a stepped pulley driven by the same driver (e.g. motor). All these approaches may achieve the common goal of minimizing or removing the indeterminacy associated with the multiple pivot joints in the end effector. Keeping the multiple joint angles close to equal may also minimize the slack that gets created due to the multi-link end effector. A combination of a scheme that that keeps the pivot angles almost equal (e.g., via passive or active means) and a scheme that takes up the slack generated by a multi-link end effector (e.g., via the proposed cam like extensions to the driving pulley), may help resolve design challenges and tradeoffs associated with multi-link articulated end effectors. The end effector can thus achieve smooth/jerk-free motion, along with high stiffness against external loads, and no backlash.

The proposed slack take-up system described herein, including the kinematic and stiff arms described above, can be configured to operate in conjunction with passive elements, such as springs, included in a transmission system. For example, springs can be used in series or in parallel with the other transmission components.

In general, to overcome the problem associated with slack generation on one side of the transmission cable in a multi-link end effector design (either on rotational DoF or two DoF), described herein are pulleys having one or more extension member (e.g., arm, wing, etc.) extending from the body of the pulley. These arms may be symmetrically configured, and may be referred to as "external" cams (as opposed to "traditional" cams) that may form an extension (e.g., rigid extension) of the driving pulley, and can be sized to take out precisely the amount of slack generated due to the kinematics of the multi-link end effector.

As mentioned above, any of the slack-compensating pulley apparatuses described herein may be a part of a cable transmission and/or a cable-driven device such as a minimal access tool. Minimal access tools may allow remote actuation of a tool by (e.g., using a cable transmission) transmitting motion from a proximal end of the tool to a distal end of the tool along an elongate length of the tool. Examples of cable-driven minimal access tools include mechanically actuated endoscopes, laparoscopes, robotic manipulators, and the like. FIGS. 24A-25D illustrate one variation of a minimal access tool. In FIG. 24A, the exemplary minimal access tool is shown in a neutral position, in which the end effector joint (a snake-like joint or multi-link joint) 2401 includes a grasper or tweezer 2405 at the distal end. One or more (e.g., two) pairs of cables may be included as part of the transmission system actuating the end effector (output) joint. For example, one pair of cables 2407 and 2409 are shown. The access tool includes an elongate body 2411 separating the end effector from a handle 2426 and frame 2416. This elongate body 2411 may be referred to as a tool shaft. The tool shaft may be cylindrical, and may be any appropriate length (e.g., greater than: 10 inches, 12 inches, 14 inches, 16 inches, 18 inches, 20 inches, 22 inches, 24 inches, 30 inches, 36 inches, etc., between κ inches and 36 inches, between 8 inches and 30 inches, etc.). In general, the tool shaft may include a proximal end and a distal end, and the proximal end of the tool shaft may be linked to the handle via an input joint. In FIG. 24A, the slack-compensating pulley 2420 is configured as a pitch axis pulley, receiving input on pitch rotation of the handle 2426; an additional slack compensating pulley may be included and configured as a yaw axis pulley (not visible in FIGS. 24A-24B, but shown 2430 in the perspective views of FIGS. 25B and 25D) and receives yaw rotation from the handle 2426. In this example, parallel kinematic connectors 2435, 2436 form the input joint may be arranged orthogonally to each other. In FIGS. 25B and 25D, the yaw axis pulley is tucked in the gap between the round ring and the pulley cover. Each connector is compliant in one direction (e.g., pitch or yaw) and rigid in another direction (e.g., yaw or pitch), and act as part of the input joint connecting the handle 2426 to the slack-compensating pulleys 2420, 2430. This arrangement isolates pitch rotation of the handle to the pitch slack-compensating pulley 2420 and yaw rotation of the handle to the yaw slack-compensating pulley 2430. The pitch slack-compensating pulley 2420 rotates about a pitch shaft 2433 that is coupled to the frame 2416, which may be coupled to a user's body (e.g., arm). Thus, the input joint between the tool shaft and the handle may receive rotational input (pitch and yaw) from a user's hand when the user grasps the handle 2426.

Figure 7:
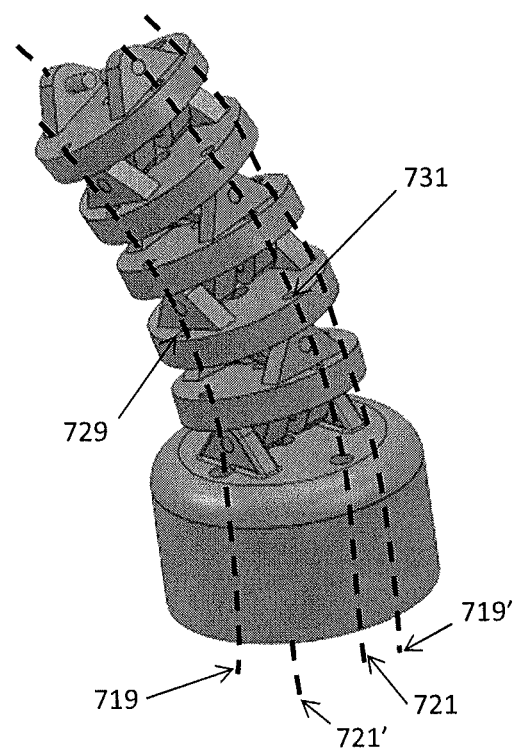
FIG. 7 shows one example of a controllably bendable elongate member comprising a snake-like end effector joint, which has multiple links, or disks, or elements that are hinged together in an alternating pattern so as to provide two rotational directions (e.g., pitch and yaw). This example may be also referred to as a "multi-link end effector joint" and may be controllably bent in pitch or yaw (or a combination of pitch and yaw) by applying and/or releasing tension on cables connected to the end link and routed through all the remaining links of the multi-link end effector. Three cables are shown (dashed lines); a fourth cable is hidden from the view.
Figure 8A:
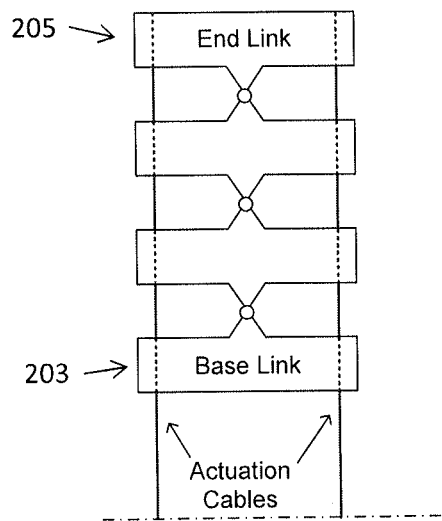
FIGS. 8A and 8B illustrate one variation of an exemplary controllably bendable member comprising a multi-link end effector joint having a single rotation that is articulated by a pair of cables connected to the end link and routed through the remaining links, in an unbent (FIG. 8A) and bent (FIG. 8B) configuration of the multi-link end effector joint.
Figure 8B:
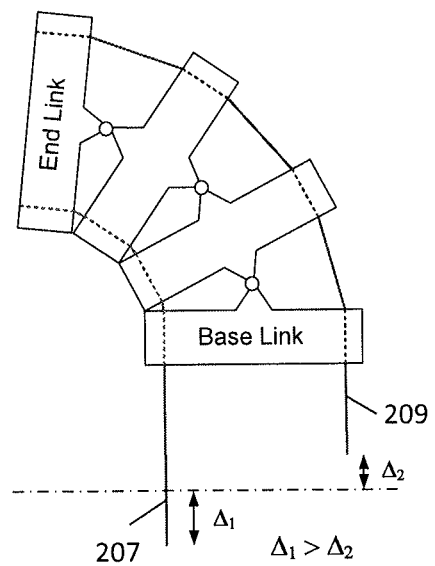

The distal end of the tool shaft 2411 may be linked to the end effector 2405 via an output joint, including a multi-link end effector joint, as described in FIG. 7, above. The output joint between the tool shaft 2411 and the end effector 2405 may provide rotational output at the end effector. The cable transmission (including the pitch and yaw slack compensating pulleys) may therefore transmit rotational movement of the handle by a user's hand to the multi-link end effector joint 2401. The transmission extending from the input joint to the output joint may include the cables 2409, 2407 and the slack-compensating pulleys 2420, 2430. In FIGS. 24A-25D, cables 2409 and 2407 are associated with pitch pulley 2420. A second pair of cables (not visible) may be associated with the other pulley (yaw pulley 2430).

Figure 25A:
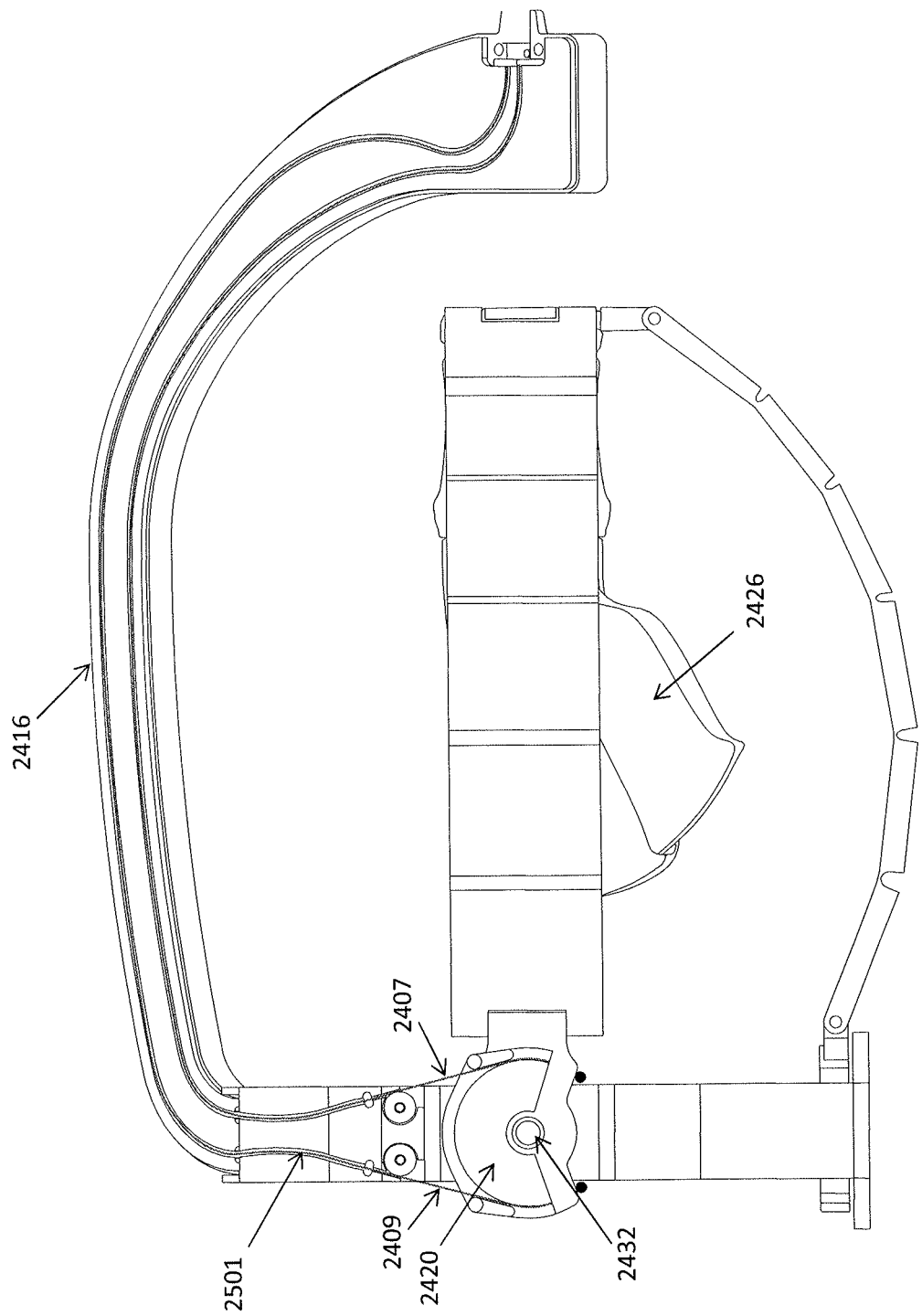
FIG. 25A is a close-up view of the handle, input joint and slack-compensating pulley of FIG. 24A in the unarticulated configuration.
Figure 25B:
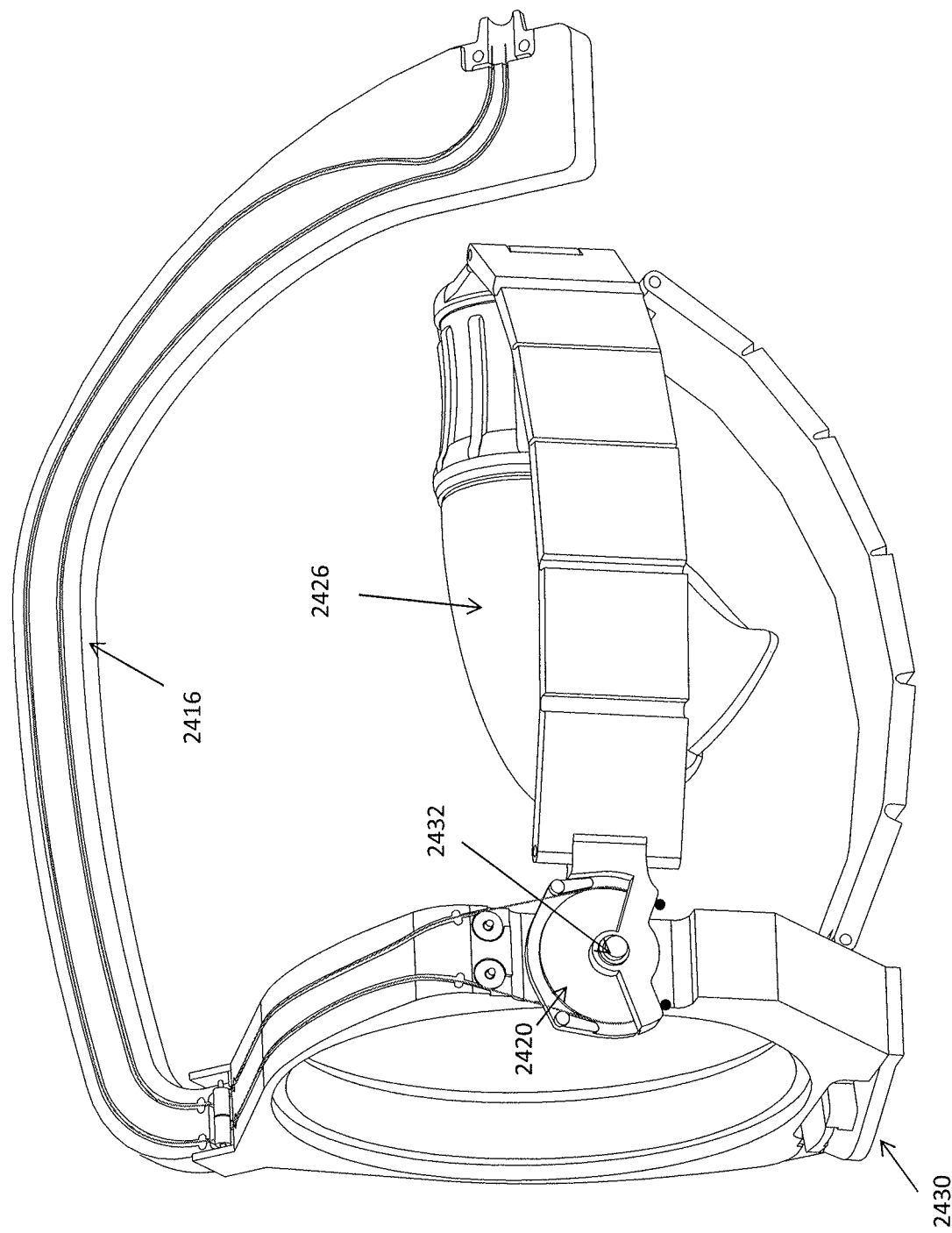
FIG. 25B is a perspective view of the close-up of FIG. 25A.
Figure 25C:
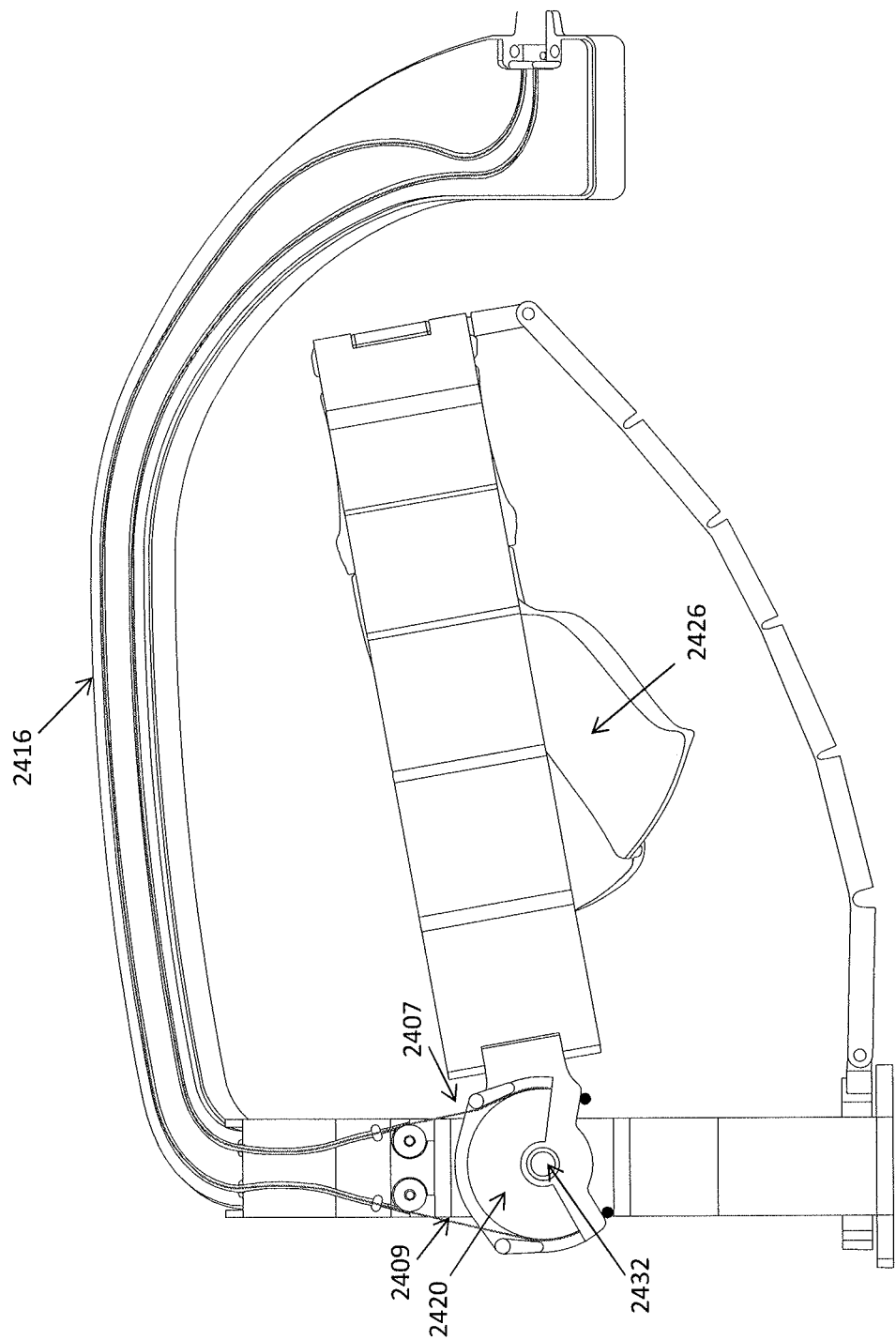
FIG. 25C is a close-up view of the handle, input joint and slack-compensating pulley of FIG. 24B in the articulated configuration.
Figure 25D:
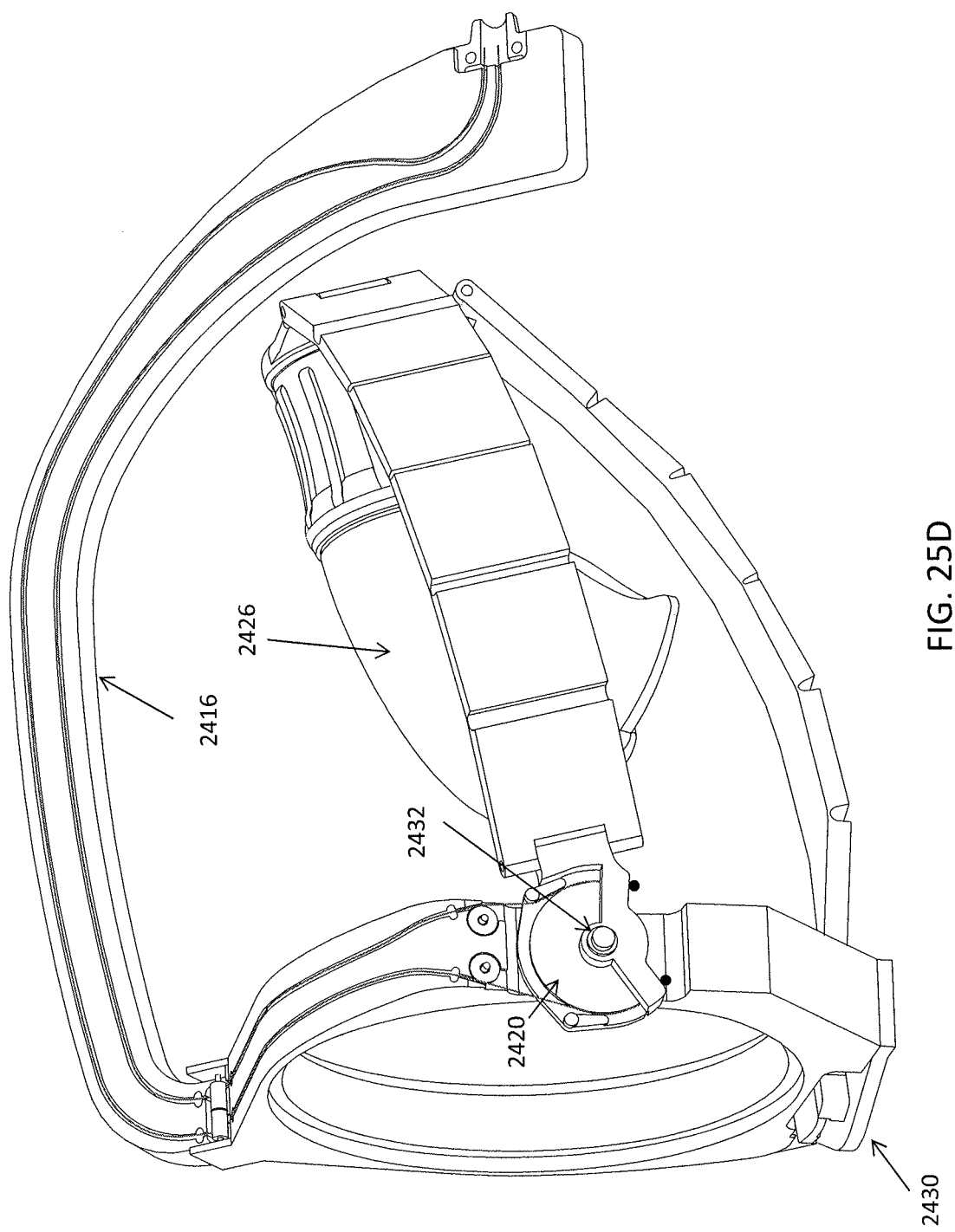
FIG. 25D is a perspective view of the close-up of FIG. 25C.

FIGS. 25A to 25D illustrate a slightly enlarged view of the proximal end of the minimal access tool shown in FIGS. 24A and 24B. In FIG. 25A, the frame includes a channel for each cable 2409, 2407 of the transmission. The cables are coupled to the slack compensating pulley 2420. The pitch slack compensating pulley 2420 is pinned to the frame by the pitch shaft 2432. The yaw slack compensating pulley 2430 is positioned orthogonally on the frame. In FIGS. 24A and 25A, the handle, and therefore the slack compensating pulleys 2420, 2430 are in a neutral position, and the end effector joint 2401 is unbent. In FIGS. 24B and 25C the distal end of the handle is pulled "up", resulting in rotation of pitch and yaw slack compensating pulleys 2420 and 2430 which separate out the pitch and yaw components.

When moving the handle to articulate the end effector in the exemplary minimal access tool shown in FIGS. 24A and 24B, the slack-compensating pulleys may prevent play, slop or backlash at the end-effector as the end effector joint is articulated by the cables. Although slack may normally be present in a cable-driven system, in this example the slack-compensating pulleys may selectively reduce or eliminate slack as described above. This is illustrated in greater detail for the apparatus of FIGS. 24A-25D in FIGS. 26A-26B.

Figure 26A:
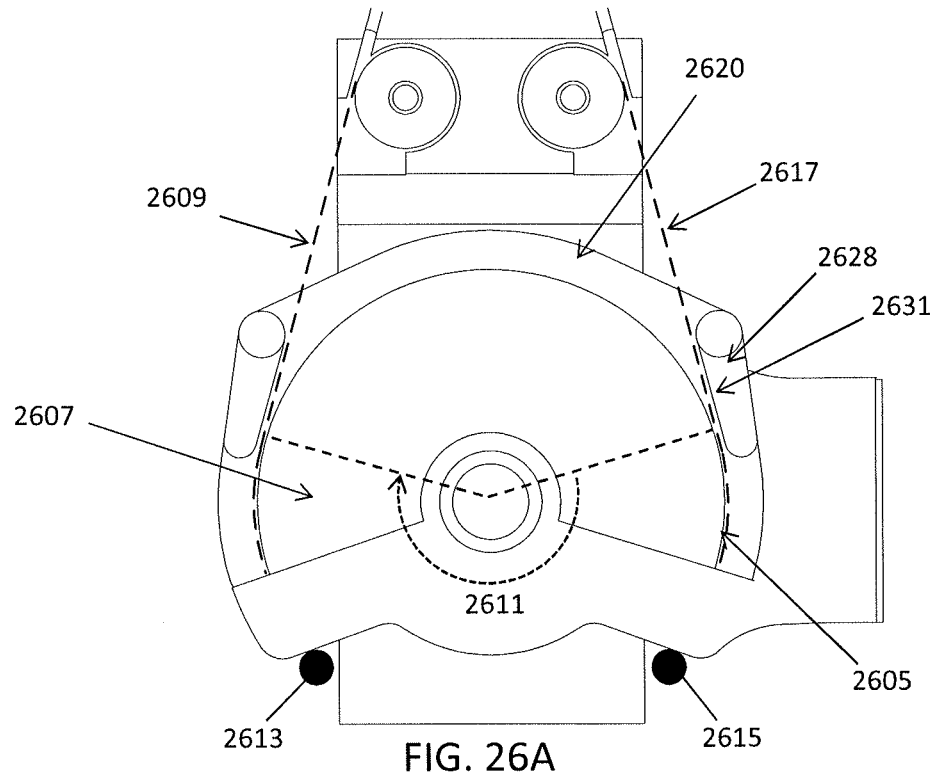
FIGS. 26A and 26B show enlarged views of the slack-compensating pulley of FIGS. 24A-25D before and after articulation, respectively, in a neutral and rotated position.
Figure 26B:
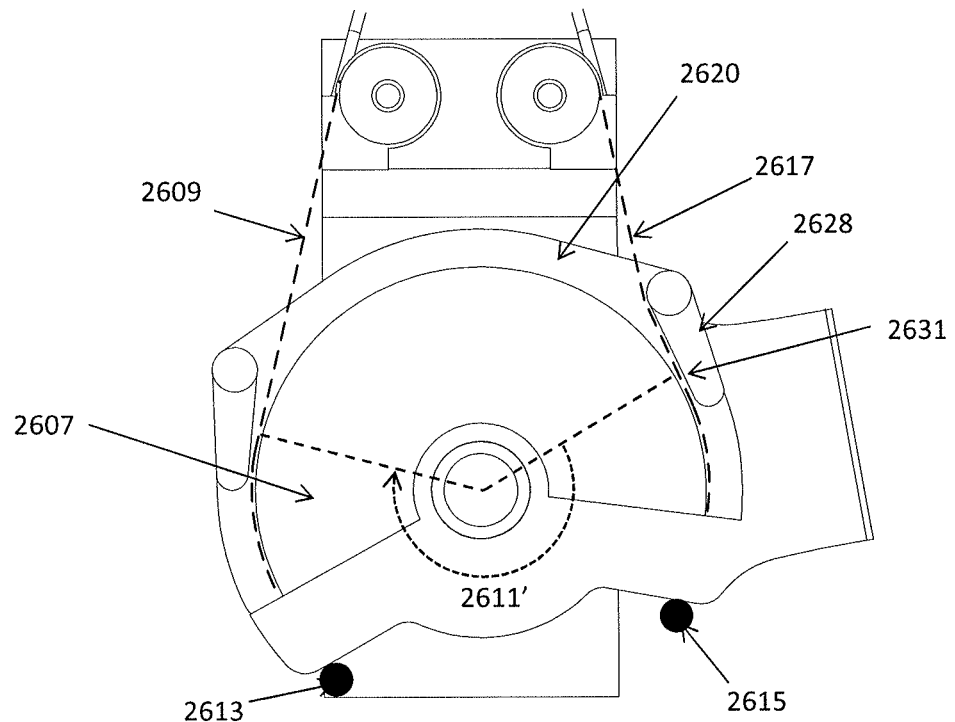

FIG. 26A show an enlarged view of the pitch slack compensating pulley of FIGS. 24A-25D. This slack-compensating pulley includes a cable track 2605 along an outer perimeter surface of the pulley body 2607 on which the theoretically single cable (comprising a first length of cable 2609 and a second length of cable 2617) wraps with a theoretical wrap angle 2611, as though these lengths formed a single cable. In this example, the first portion 2609 is tethered to the pulley body by a lock 2613 and the second cable portion 2617 is attached on the other side of the pulley body and is also locked via 2615 to the pulley body. The slack-compensating cable includes a support 2620 extending from the pulley body 2607 that is rigidly connected to the pulley body so that the two rotate together. A slack take-up surface 2631 is present on the support 2628. In this example, the slack-take up surface 2631 is the surface of the paddle-shaped protrusion from the support 2620. The slack take-up surface 2631 is positioned radially further outward than a nearest region of the surface of the pulley body so that the cable 2617 passes between the pulley body 2607 and the slack take-up surface 2631. As shown by the transition from FIG. 26A to 26B, the support and slack take-up surface rotate with the pulley body to remove and/or reduce slack in the cable when the pulley body is rotated in a first direction by increasing the wrap angle 2611' and the path length taken by the portion of the cable 2617 as it extends off of the pulley body. Note that the wrap angle 2611 is measured for the entire pulley, between contact points for the incoming length of cable 2609 and the outgoing length of cable 2617, irrespective of whether a continuous cable is actually wrapped around the pulley body, or if the cable comprises separate tethered or anchored lengths, as shown in FIGS. 26A and 26B.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A slack-compensating pulley apparatus for a cable transmission system, the slack-compensating pulley apparatus comprising:

a pulley body;

a cable track along a surface of the pulley body on which a cable may wrap with a wrap angle;

a support rigidly coupled to the pulley body and extending from the pulley body; and a slack take-up surface on the support, wherein the slack take-up surface is positioned radially outside of the surface of the pulley body so that a length of cable may extend between the pulley body and the slack take-up surface, wherein the support and slack take-up surface rotate with the pulley body to remove slack in the cable when the pulley body is rotated in a first direction by increasing the wrap angle of the cable on the pulley body.

2. The slack-compensating pulley apparatus of claim 1, further comprising a second slack take-up surface, wherein the second slack take-up surface is positioned radially outside of the surface of the pulley body so that a second length of cable may extend between the pulley body and the second slack take-up surface, wherein the second slack take-up surface rotates with the pulley body to remove slack in the cable when the pulley body is rotated in a second direction.

3. The slack-compensating pulley apparatus of claim 1, further comprising a second slack take-up surface on the support, wherein the second slack take-up surface is positioned radially outside of the surface of the pulley body so that a second length of cable may extend between the pulley body and the second slack take-up surface, wherein the support and second slack take-up surface rotate with the pulley body to remove slack in the cable when the pulley body is rotated in a second direction.

4. The slack-compensating pulley apparatus of claim 1, further comprising a cable on the surface of the pulley body, the cable having a first cable length extending in a first cable path that is tangent to the surface of the pulley body on a first side of the pulley body, wherein when the slack take-up surface rotates with the pulley body about an axis of rotation in the first direction, the slack take-up surface is driven onto the first cable length on the first side of the pulley body and deflects the first cable length from the first cable path into a longer path, and when the pulley body is rotated in the axis of rotation in a second direction, the slack take-up surface is withdrawn away from the first cable length on the first side of the pulley body to shorten the cable path.

5. The slack-compensating pulley apparatus of claim 1, wherein the support comprises an arm or wing extending from the pulley body.

6. The slack-compensating pulley apparatus of claim 1, wherein the pulley body is circular.

7. The slack-compensating pulley apparatus of claim 1, wherein the cable track extends partially around the pulley body.

8. The slack-compensating pulley apparatus of claim 1, wherein the slack take-up surface is an inner surface of a loop formed by the support.

9. The slack-compensating pulley apparatus of claim 1, wherein the support comprises a plate extending from the pulley body parallel to and offset from a plane through the cable track.

10. The slack-compensating pulley apparatus of claim 1, wherein the support comprises a bias element configured to allow the slack take-up surface to deflect relative to the pulley body when force is applied against the slack take-up surface by the cable.

11. The slack-compensating pulley apparatus of claim 1, wherein the slack take-up surface is rigidly connected to the support and rotates in the first direction with the pulley body when the pulley body is rotated in the first direction.

12. A slack-compensating pulley apparatus for a transmission system, the slack-compensating pulley apparatus comprising:

a pulley body;

a cable track along a surface of the pulley body on which a cable may wrap;

a support comprising a plate rigidly coupled to the pulley body and extending from the pulley body parallel to and offset from a plane through the cable track; and a protrusion comprising a slack take-up surface, the protrusion extending from the support, wherein the slack take-up surface is positioned radially outside of the surface of the pulley body so that a length of cable may extend between the pulley body and the slack take-up surface, wherein the support and the slack take-up surface rotate with the pulley body to remove slack in the cable when the pulley body is rotated in a first direction by lengthening a path taken by the cable.

13. The slack-compensating pulley apparatus of claim 12, further comprising a second slack take-up surface, wherein the second slack take-up surface is positioned radially outside of the surface of the pulley body so that a second length of cable may extend between the pulley body and the second slack take-up surface, wherein the second slack take-up surface rotates with the pulley body to remove slack in the cable when the pulley body is rotated in a second direction by lengthening a path taken by the cable.

14. The slack-compensating pulley apparatus of claim 12, further comprising a cable on the cable track of the surface of the pulley body, the cable having a first cable length extending in a first cable path that is tangent to the surface of the pulley body on a first side of the pulley body, wherein when the slack take-up surface rotates with the pulley body about an axis of rotation in the first direction the slack take-up surface deflects the first cable length from the first cable path into a longer cable path to remove slack, and when the pulley body is rotated in the axis of rotation in a second direction, the slack take-up surface is withdrawn away from the first cable length so that the first cable length extends in a shorter cable path.

15. The slack-compensating pulley apparatus of claim 12, wherein the pulley body is circular.

16. The slack-compensating pulley apparatus of claim 12, wherein the cable track extends partially around the pulley body.

17. The slack-compensating pulley apparatus of claim 12, wherein the support comprises a bias element configured to allow the slack take-up surface to deflect relative to the pulley body when force is applied against the slack take-up surface by the cable.

18. The slack-compensating pulley apparatus of claim 12, wherein the slack take-up surface is rigidly connected to the support and rotates in the first direction with the pulley body when the pulley body is rotated in the first direction.

19. A slack-compensating pulley apparatus for a transmission system, the slack-compensating pulley apparatus comprising:

a pulley body having an axis of rotation;

a cable wrapped around an outer surface of the pulley body at a wrap angle and having a first cable length extending in a first cable path that is tangent to the outer surface of the pulley body on a first side of the pulley body;

a support rigidly coupled to the pulley body and extending from the pulley body; and a slack take-up surface on the support, wherein the slack take-up surface rotates with the pulley body so that when the pulley body is rotated about the axis of rotation in a first direction, the slack take-up surface is driven against the first cable length and deflects the first cable length from the first cable path into a longer path, increasing the wrap angle on the pulley body and removing slack, and when the pulley body is rotated in the axis of rotation in a second direction, the slack take-up surface is withdrawn away from the first cable length so that the first cable length travels in a shorter cable path reducing the wrap angle on the pulley body.

20. The slack-compensating pulley apparatus of claim 19, further comprising a second slack take-up surface, wherein the second slack take-up surface rotates with the pulley body so that when the pulley body is rotated about the axis of rotation in the second direction, the second slack take-up surface is driven against a second cable length on a second side of the pulley body extending in a second cable path that is tangent to the outer surface of the pulley body on the second side of the pulley body, so that the second slack take-up surface deflects the second cable length from the second cable path into a longer path, and when the pulley body is rotated in the axis of rotation in the first direction, the second slack take-up surface is withdrawn away from of the second cable length so that the second cable length travels in a shorter cable path.

21. The slack-compensating pulley apparatus of claim 19, wherein the support comprises an arm or wing extending from the pulley body.

22. The slack-compensating pulley apparatus of claim 19, wherein the pulley body is circular.

23. The slack-compensating pulley apparatus of claim 19, wherein the cable track extends partially around the pulley body.

24. The slack-compensating pulley apparatus of claim 19, wherein the slack take-up surface is an inner surface of a loop formed by the support.

25. The slack-compensating pulley apparatus of claim 19, wherein the support comprises a plate extending from the pulley body parallel to and offset from a plane through the cable track.

26. The slack-compensating pulley apparatus of claim 19, wherein the support comprises a bias element configured to allow the slack take-up surface to deflect relative to the pulley body when force is applied against the slack take-up surface by the cable.

27. The slack-compensating pulley apparatus of claim 19, wherein the slack take-up surface is rigidly connected to the support and rotates about the axis of rotation in the first direction with the pulley body when the pulley body is rotated in the first direction and about the axis of rotation in the second direction with the pulley body when the pulley body is rotated in the second direction.

* * * * *